(12) United States Patent
Valentini et al.

(10) Patent No.: US 6,837,851 B1
(45) Date of Patent: Jan. 4, 2005

(54) ADJUSTABLE SURGICAL RETRACTOR

(75) Inventors: Valerio Valentini, Montreal (CA);
Anthony Paolitto, Montreal (CA);
Raymond Cartier, Montreal (CA)

(73) Assignee: Coroneo, Inc., Montreal (CA)

( * ) Notice: Subject to any disclaimer, the term of this patent is extended or adjusted under 35 U.S.C. 154(b) by 0 days.

(21) Appl. No.: 10/110,195

(22) PCT Filed: Oct. 18, 2000

(86) PCT No.: PCT/CA00/01230

§ 371 (c)(1),
(2), (4) Date: Apr. 17, 2002

(87) PCT Pub. No.: WO01/28431

PCT Pub. Date: Apr. 26, 2001

(30) Foreign Application Priority Data

Oct. 18, 1999 (CA) .............................................. 2286929

(51) Int. Cl.[7] ................................................ A61B 1/32
(52) U.S. Cl. ..................................................... 600/210
(58) Field of Search ................................ 600/210, 214, 600/215, 216, 218, 219, 220, 224, 225, 235; 623/2.11; 606/206, 207, 208

(56) References Cited

U.S. PATENT DOCUMENTS

| | | | | |
|---|---|---|---|---|
| 58,969 A | * | 10/1866 | Ashley | 81/3.41 |
| 761,821 A | * | 6/1904 | Clark et al. | 600/224 |
| 3,750,652 A | * | 8/1973 | Sherwin | 606/90 |
| 4,655,218 A | * | 4/1987 | Kulik et al. | 606/207 |
| 5,178,133 A | * | 1/1993 | Pena | 600/203 |
| 5,476,510 A | * | 12/1995 | Eberhardt et al. | 623/2.11 |
| 5,618,260 A | * | 4/1997 | Caspar et al. | 600/210 |
| 5,755,661 A | * | 5/1998 | Schwartzman | 600/216 |

* cited by examiner

*Primary Examiner*—Eduardo C. Robert

(57) ABSTRACT

A surgical tool for retracting body tissue during surgery consisting of two pivoting arms each provided with a finger, a translating actuation member also provided with a finger, and a single actuator mechanically coupled to either one of the pivoting arms or the translating actuation member. The two pivoting arms and the actuation member are operatively connected together for simultaneous movement between a closed configuration having the three fingers close together, and an open configuration having the three fingers spaced apart. The surgical tool is adaptable to suit the specific patient anatomy and desired degree of tissue retraction.

29 Claims, 22 Drawing Sheets

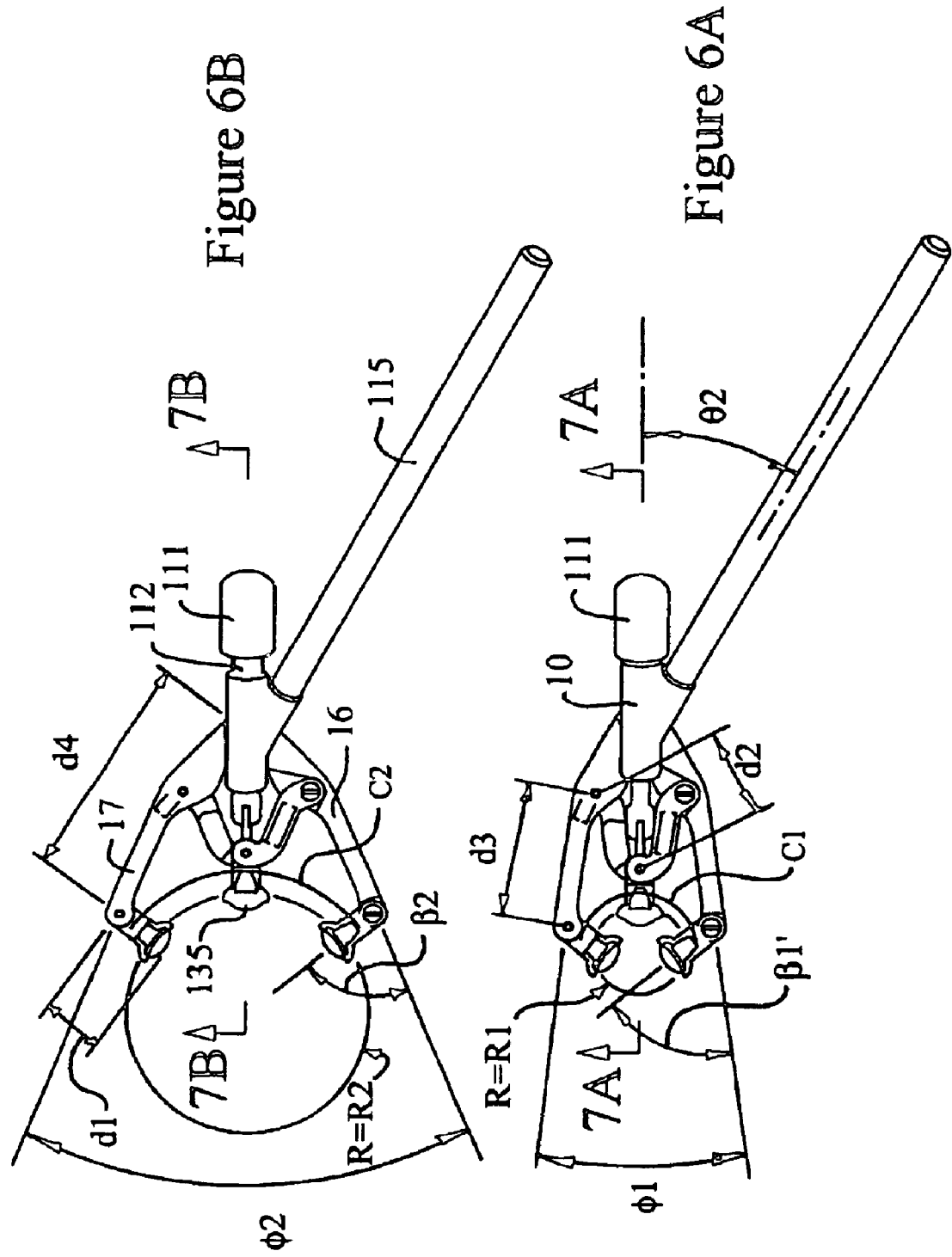

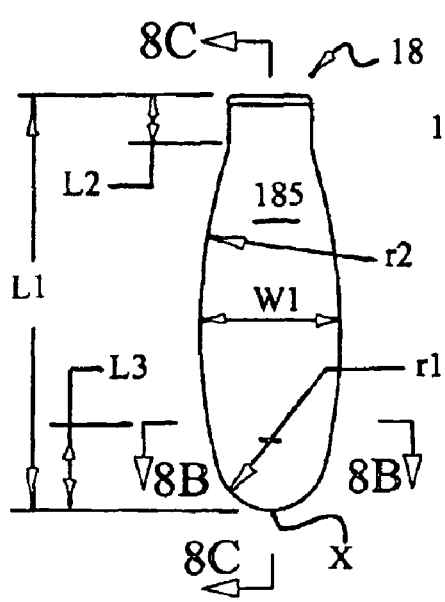
Figure 8A
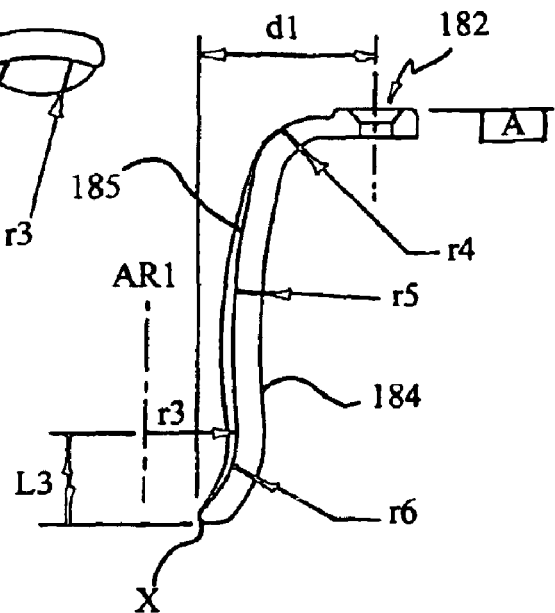
Figure 8B  Figure 8C
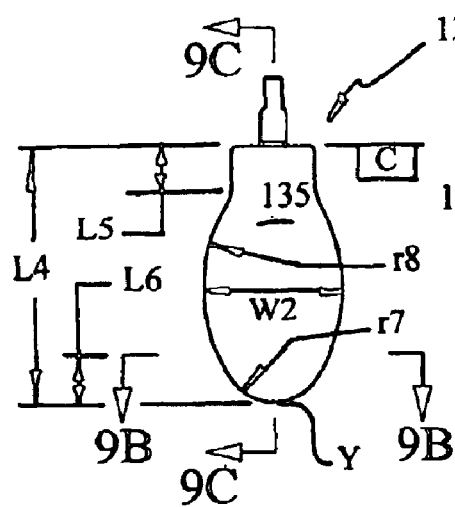
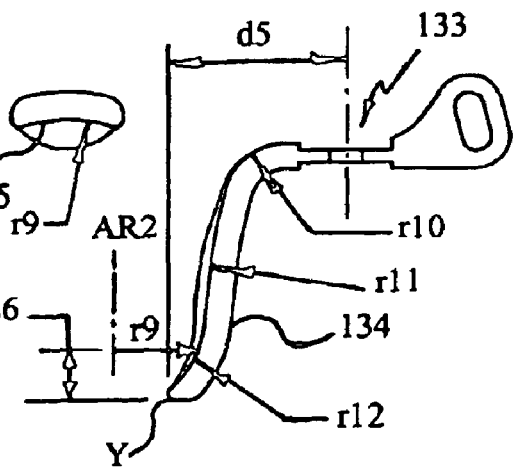
Figure 9A  Figure 9B  Figure 9C

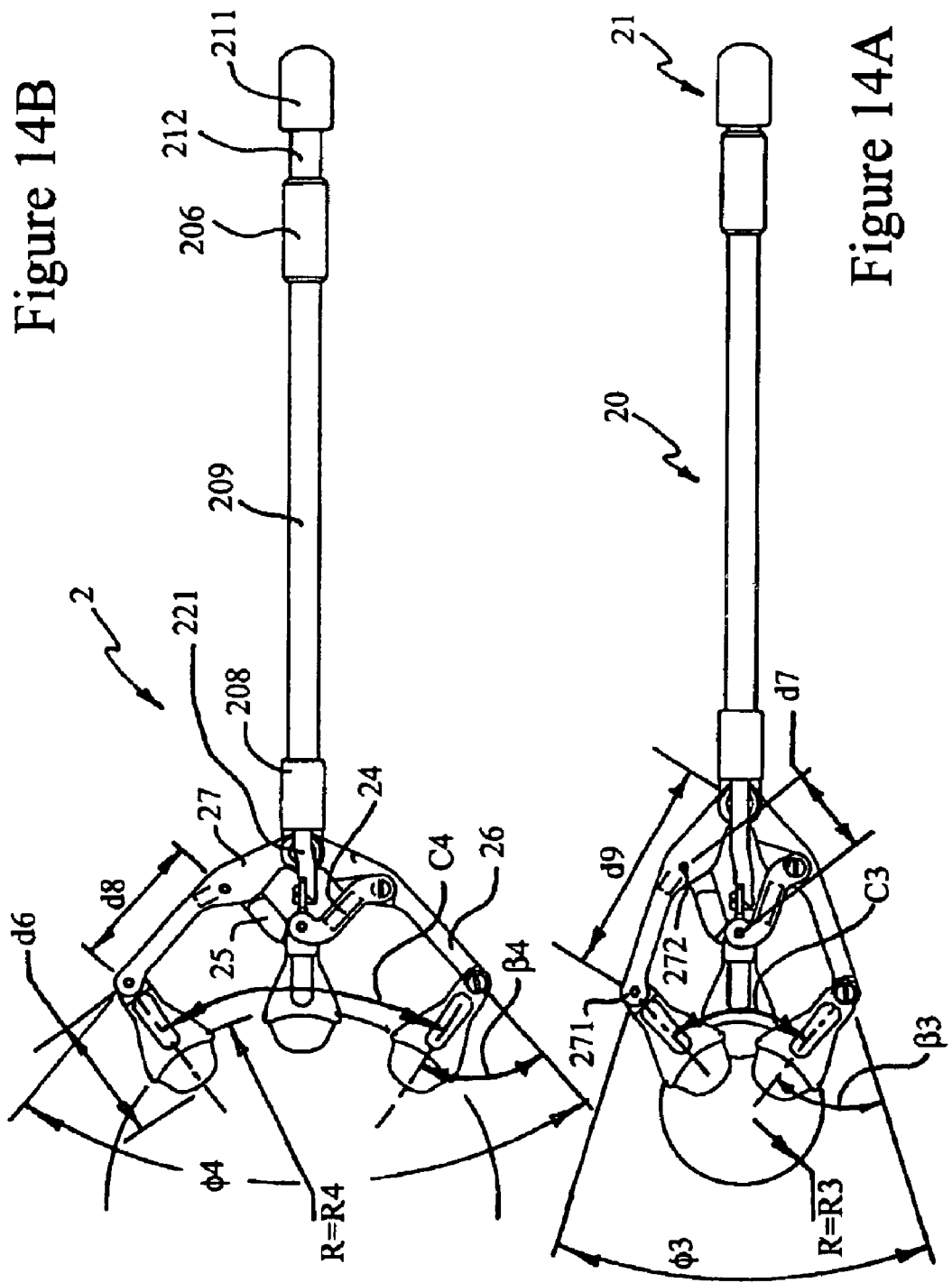

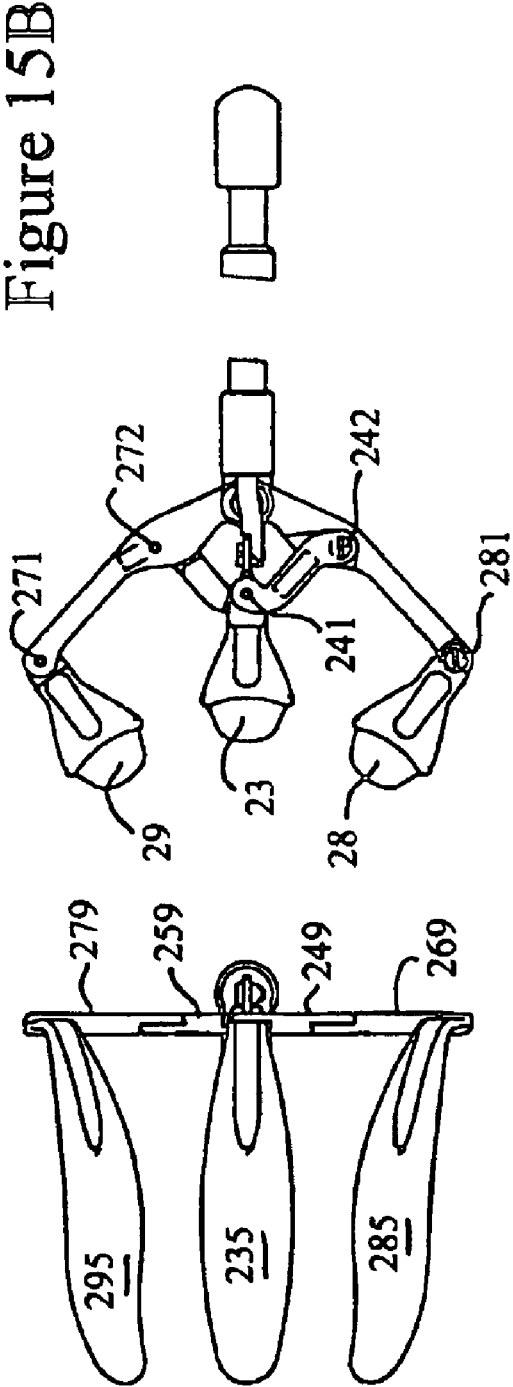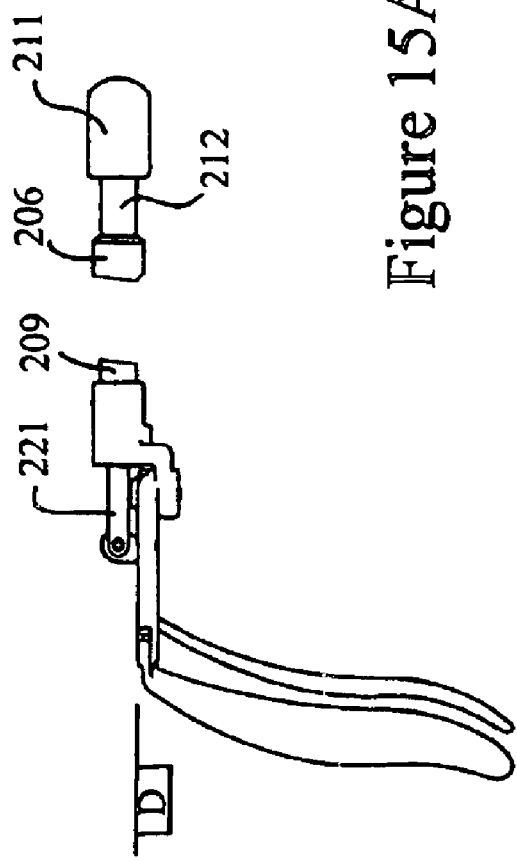

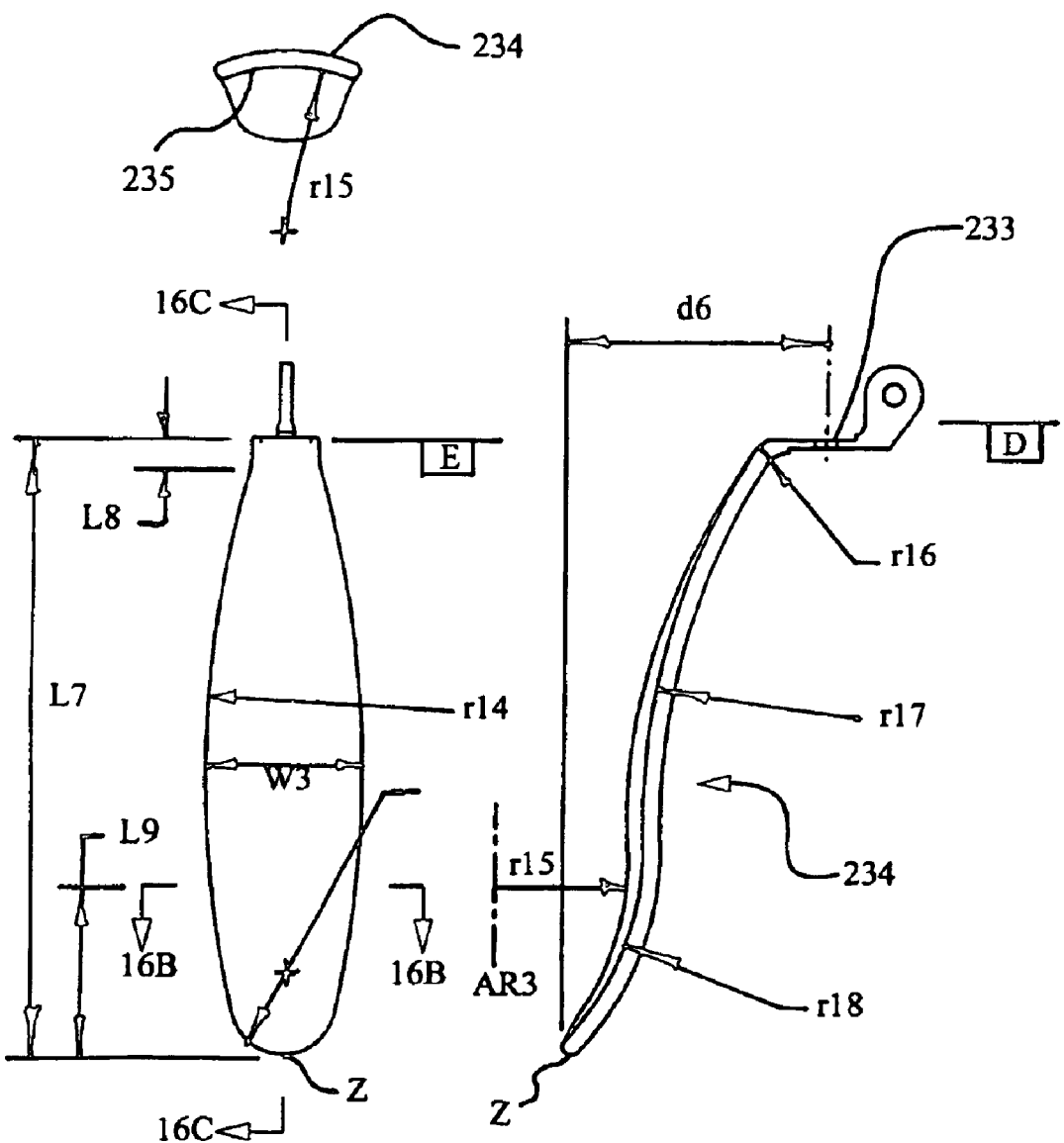

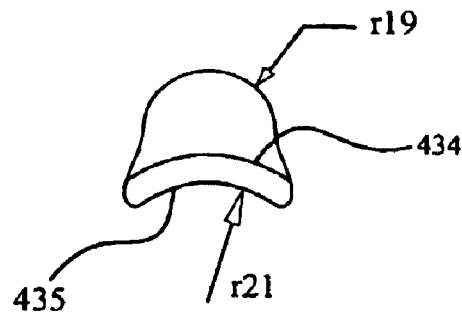
Figure 17B
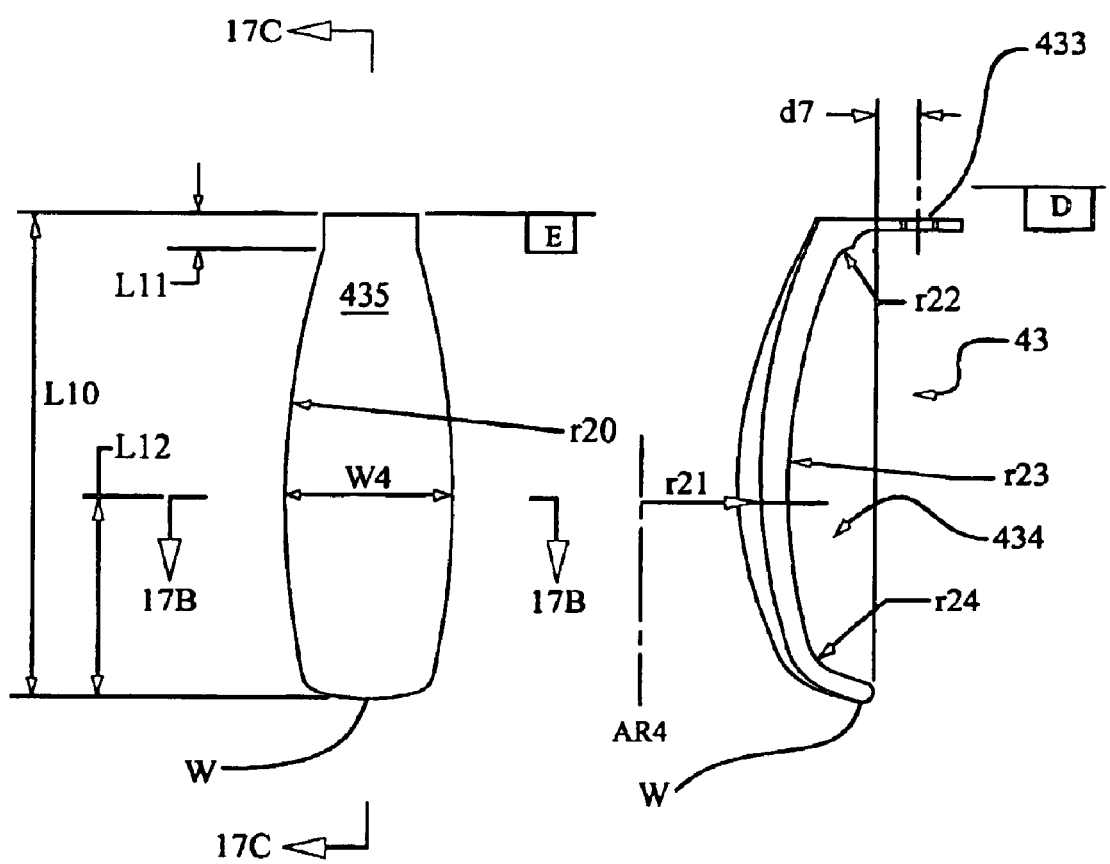
Figure 17A
Figure 17C

ADJUSTABLE SURGICAL RETRACTOR

FIELD OF THE INVENTION

The present invention relates to the field of cardiac surgery apparatus and more specifically, to valve surgery apparatus for performing valve repair or valve replacement interventions.

BACKGROUND OF THE INVENTION

Valve surgery includes interventions where a cardiac valve is repaired, for instance with valve decalcification interventions or annuloplasty for atrioventricular valves. Alternatively, valve surgery may also involve interventions where the entire diseased valve is either replaced by a mechanical valve, a synthetic valve or bioprosthesis valve such as one derived from a porcine heart valve. The aortic or mitral valve is most commonly involved in valve surgery interventions.

Traditional valve surgery has been commonly performed through a midline sternotomy incision, where the patient's sternum is incised and the ribcage retracted to obtain access to the patient's heart and major blood vessels.

More recently, in minimally invasive procedures smaller parasternal incisions (mini-sternotomy) or intercostal thoracotomy approaches have also been employed. In thoracotomy approaches, two adjacent ribs are spread apart, at times even removing a length of rib to improve access into the patient's thorax and to the patient's heart. In both approaches, a chest retractor is used to spread apart the patient's skin and thoracic bone structure to maintain an incised opening or surgical window onto the underlying cardiac tissue.

Chest retractors exist in many sizes and shapes and have been present since the dawn of cardiac surgery. Most known chest retractors have an elongate rack bar and two retracting arms, namely a fixed retracting arm and a movable retracting arm. Both arms typically extend in a direction normal to the rack bar. The movable arm can be displaced along the rack bar, and relative to the fixed arm, by using a crank to activate a pinion mechanism which engages teeth on the rack bar. Two blades are provided, usually disposed below the retractor arm and extending into the surgical incision, to interface with the patient's skin and thoracic bone structure. These two blades apply the retraction that creates the surgical window by the relative movement and an ensuing spacing apart of the two retractor arms.

Traditional valve surgery has been performed with the support of a heart-lung machine, whereby the patient's blood is oxygenated outside the body through extracorporeal circulation (ECC) and the heart is arrested through administration of cardioplegia. This allows the surgeon to safely pierce and penetrate a heart chamber or a major heart vessel in order to perform a surgical intervention while the patient's blood flow is diverted and bypassed to the heart-lung machine. A series of cannulae and catheters are usually employed to divert the patients blood flow to the heart-lung machine for cardiopulmonary bypass and to return the oxygenated blood to the aorta. The aorta is cross clamped to avoid backflow into the heart chambers and surgical field. In aortic valve surgery, the aorta is cannulated for arterial return (aortic cannulation) usually at the pericardial reflection. Venous drainage is obtained by a cannula placed in the right atrial appendage (right atrial cannulation). A cannula serving to perfuse the arrested heart with cardioplegia solution during the surgical intervention is usually placed in the right atrium and directed into the coronary sinus (retrograde cardioplegia cannula). Mitral valve surgery has traditionally been performed with superior and inferior vena cavae cannulation (bicaval cannulation) and aortic cannulation. These cannulae and catheters are introduced into some cardiac tissue through the surgical window and tend to occupy the surgical workspace.

Subsequent to the creation of a surgical window through the patient's skin and thoracic bone structure, and following the placement of the patient on ECC, the great majority of valve surgery procedures involve some form of surgical incision of cardiac tissue and subsequent retraction of incised cardiac tissue to access the diseased heart valve. Cardiac tissue includes pericardium, epicardium, myocardium, endocardium, tissue of the septal wall, aorta tissue, vena cava tissue, cardiac valves, heart muscle, the coronary arteries and veins, the pleurae, the thymus, and other like anatomical tissue.

In traditional aortic valve surgery, surgical access to the diseased aortic valve is mostly achieved through a surgical incision in the aorta. An oblique incision (aortotomy) around a portion of the aorta's circumference is made in the segment of aorta between the aortic valve (AV) and the aortic surgical cross clamp (ACC). Alternatively, other like means of restricting backflow through the aorta, such as an intraluminal occluding balloon catheter, may also be used.

Following the aortotomy, three traction stay sutures (TSS) are usually placed through the commissures of the valvular annulus and suspended from surgical drapes under tension. A portion of these drapes is usually placed between the chest retractor blades and the patient's skin and bone structure along the sternotomy incision. Alternatively, the stay sutures may be anchored to the patient's surrounding cardiac tissue or to the chest retractor. In addition to stay sutures, a variety of hand held tissue retractors (HHR) are also deployed throughout the surgical intervention and used to help improve access to the aortic valve by displacing aortic tissue generally along the aortotomy incision (see FIG. 18). The valve annulus may then be carefully debrided of calcific deposits and, if required, the native valve is excised and replaced.

Surgical access to a diseased mitral valve (MV) is mostly achieved through a surgical incision of the left atrium. To attempt to achieve optimal exposure, the heart is elevated out of the chest and rotated, allowing the apex to drop posteriorly while elevating the right side of the heart. This maneuver tends to bring the posterior mitral valve leaflet towards the right side of the patient in a plane which tends to face the surgeon, often permitting better visualization of the mitral valve and subvalvular structures.

Following the median sternotomy, the pericardium is opened slightly to the right of the midline and the right side of the pericardium is sutured under tension to the chest wall to help provide the elevation of the right side of the heart. The pericardial edges on the left side of the incision are not suspended. After bicaval cannulation, the superior vena cava is usually mobilized by incising the pericardium above it. A tourniquet is often placed on the inferior vena cava and traction is applied in a general direction toward the patient's feet. This procedure further helps to elevate the right side of the patient's heart. The left atrium is generally incised parallel to the intra-atrial groove. This incision is usually extended below the superior vena cava and a considerable distance below the inferior vena cava.

Current known types of retractor systems for mitral valve surgery, usually with three tissue retractors each individually secured to a chest retractor, are used to maintain the exposure to the mitral valve through the left atrial incision (see FIGS. 19A and 19C). The operating table is usually also rotated away from the surgeon to improve visibility.

Due to the limitations of these current retractor systems, exposure of the mitral valve often requires additional maneuvers. Pledgetted stay sutures (PSS) may be placed through the mitral valve annulus at either commissure and traction exerted to help pull the mitral valve towards the surgeon.

Recently, with the advent of less invasive procedures, the mitral valve may also be accessed through a transeptal approach via the right atrium (see FIG. 20). After the aorta is cross clamped and cardiac arrest achieved with cardioplegia, the right atrium is incised first. Four traction stay sutures (TSS) are generally placed to keep right atrium open. The intra-atrial septum is subsequently incised to obtain access to the left atrium and the mitral valve. Typically, 2–3 pledgetted mattress sutures (PMS) are placed in the intra-atrial septum and traction is subsequently applied. This retracts the intra-atrial septum and enhances visualization of the mitral valve.

Hand held retractors (HHR) are engaged with the intra-atrial septum with an aim to improve exposure. Typically, at least two hand held retractors are used. One is placed in the superior portion of the left atrium along the intra-atrial septum incision, and pulled towards the patient's head or left shoulder. The other is placed in the inferior portion of the left atrium along the intra-atrial septum incision, and pulled towards the patient's feet or left foot. Tending to further facilitate exposure of the mitral valve, a Harrington retractor (HAR) is placed in the left atrium along the right side of the intra-atrial septum incision, and traction applied laterally towards the surgeon (i.e. towards the patient's right side). This often helps deliver the mitral valve into direct view of the surgeon. The surgical intervention on the mitral valve is at this point performed. The mitral valve mechanism is usually tackled first, after which a valvular annuloplasty is generally performed.

Current aortic and mitral valve surgeries described above may in some instances be characterized by a number of associated drawbacks as will be described in greater detail below.

The installation of traction stay sutures, used to retract cardiac tissue during valve surgery, may be a time-consuming process given the relatively high number of such sutures generally required and since the securing of said stay sutures through manual tying of the suture line is a multi-step threading and knotting procedure. Current mitral valve surgery may generally require 6–8 stay sutures; 4 current aortic valve surgeries may require 3–5 stay sutures.

The installation of traction stay sutures may at times be cumbersome given the limited space or poor access during the manual tie down of the suture line lengths, especially in surgical interventions where the surgical window is small.

Once the traction stay sutures have been placed, they are not conducive to allowing readjustment in either the retraction tensile load they apply on the cardiac tissue, or in the vector direction of the retraction load they apply. To readjust the retraction load or direction vector, the surgeon must untie and retie the suture line lengths or cut the existing suture line and replace it with a new suture that will be secured in a manner to exert the desired retraction load and direction vector on the cardiac tissue. Generally, adjustment of the desired tensile retraction by cutting an existing suture line and re-piercing a new suture line is not desirable. A re-piercing of the cardiac tissue with a subsequent suture tends to increase the likelihood of inducing tissue trauma or tissue tearing which may have to be surgically repaired.

At times, the vector direction of retraction that is achievable with stay sutures may be limited by the availability of anchoring points, or tie down points, for the stay suture. Anchoring points or tie down points, either in surrounding cardiac tissue or on the chest retractor, may not be present in a location that would enable the resultant traction direction to be the desired direction. Consequently, additional sutures are needed in order that a desired retraction direction vector is achieved by the sum of two or more stay sutures whose vector retraction directions yield a desired direction vector on the cardiac tissue.

Traction stay sutures tend to exert a concentrated load on the cardiac tissue. This may at times lead to tissue tearing. To redistribute these concentrated loads, pledgets are sometimes placed between the suture and the cardiac tissue in order to minimize the likelihood of tissue tearing. During removal of pledgetted traction stay sutures, it may be possible to unintentionally leave the pledget behind within the heart chamber which may lead to complications such as stroke or infarct if said pledget is not retrieved.

During aortic valve surgery, three traction stay sutures are usually installed, each one placed at the top of each commissure. This tends to result in a non-circular opening in the incised aorta perimeter which may interfere with the excision of the existing valve, or the sizing and installation of a new replacement valve. Consequently, hand held tissue retractors may also be deployed between two stay sutures, each engaged with aortic tissue, to attempt to render this opening more circular. In certain cases, these discrete concentrated loads from the traction sutures may tend to bend the aorta along its flow axis thereby distorting the aorta wall to collapse its diameter at the bend location, since there is insufficient support in tending to maintain the aorta circumference.

Valve replacement surgeries or annuloplasty surgeries are generally characterized by the high number of securing sutures placed through the valve annulus and either the annuloplasty ring annulus or the valve prosthesis annulus. As such, there tends to be an increased risk of suture tangling as the number of traction stay sutures required increases.

The use of hand held tissue retractors in valve surgery are also characterized by a number of associated drawbacks as will be described in greater detail below. Two to three hand held tissue retractors are typically used in current mitral valve surgeries and current aortic valve surgeries. Hand held tissue retractors must be held by the surgeon assistant or nurse. In addition to being a poor use of the surgeon assistant's time and abilities, hand held retractors make for an unstable surgical site since the retractors tend not to be kept still and motionless in the exact same position for extended periods of time. This may compromise the outcome of the surgery during delicate interventions which prefer a very stable surgical site.

Although available in a number of discrete sizes, hand held retractors are typically of fixed geometry. This tends to result in a compromised fixed tool configuration being employed on differing patient anatomies.

The use of chest-retractor-mounted tissue retractors in valve surgery is also characterized by a number of associated drawbacks, as will be described in greater detail below.

Current known retractor systems for mitral valve surgery performed through a left atrium approach may require as many as three chest-retractor-mounted tissue retractors (CRM). Tissue retractors generally consist of a tissue-engaging portion, blade or rake attached to a shaft which is secured to a chest retractor at the shaft free end. The high number of clamps and mounting rods associated with each of the three tissue retractors tends to make for a high part count and timely surgical set-up. Moreover, the high number of tissue retractors and associated mounting rods and clamps may, in certain instances, render the surgical space very cluttered and non-ergonomic.

Another limitation of some current valve surgery retractor systems is that the proximal shaft end of a tissue retractor is usually secured to the top of a chest retractor arm (FIG. 19C), or to a mounting rail substantially parallel to and slightly above a chest retractor arm (FIG. 19A). Consequently, the vector pull direction of an imposed retraction load on a cardiac tissue, which is generally substantially in line with the shaft axis of the tissue retractor, generally extends from the engaged cardiac tissue to a mounting point for the proximal shaft end of the tissue retractor on a chest retractor arm (or slightly above a chest retractor arm). The tops of the deployed chest retractor arms, which maintain a surgical window, generally form a substantially horizontal plane (when the patient is placed in a supine horizontal position on a surgical table). The farther an engaged cardiac tissue is from a deployed chest retractor arm where the proximal shaft end of the tissue retractor will be mounted, the more horizontal is the direction of the imposed tissue retraction load and of the tissue retractor shaft axis. The closer an engaged cardiac tissue is to a deployed chest retractor arm where the proximal shaft end of the tissue retractor will be mounted, the more vertical is the direction of the imposed tissue retraction load and of the tissue retractor shaft axis. Therefore, once the desired cardiac tissue is engaged by a tissue retractor, in some known current retractor systems the vector pull direction tends to be a resultant predetermined vector set by the mounting location of the proximal shaft end of the tissue retractor on the chest retractor. For instance, it may be very difficult to impose a vertical pull vector on an engaged cardiac tissue with some current valve surgery retractor systems. Furthermore, in some current known valve retractor systems, because the tissue-engaging portion, blade or rake is in a rigid fixed configuration relative to its tissue retractor shaft, and because the shaft is generally limited to being mounted to a chest retractor arm (or to a mounting rail parallel to and slightly above the chest retractor arm), the orientation of the tissue-engaging portion, blade or rake relative to its position within a surgical window is a substantially fixed result except for the free rotation of the tissue-engaging blade about the centerline of its shaft (if a round shaft is used). As a result, these current valve retractor systems may be able to place the tissue-engaging portion, blade or rake in many positions within a surgical window, but the orientation of the said portion at any such given position is greatly limited by the location on the chest retractor perimeter where the proximal shaft end is eventually mounted.

At times, in order to provide the desired traction vector on a cardiac tissue, the proximal shaft end of the tissue retractor must be secured in a location too far away from a mounting clamp available on the chest retractor. Bringing the proximal shaft end to the location of the mounting clamp available on the chest retractor where it can subsequently be secured, may result in a compromised traction vector. Consequently, one or more additional co-operating tissue retractors must also be deployed such that the desired traction vector is obtained through the vector sum of the additional tissue retractor traction vector and the initial compromised traction vector. This tends to lead to more parts required to achieve the desired tissue retraction and consequently a more cluttered surgical workspace.

In process re-adjustments of the tissue retractors in some known valve surgery systems may at times prove fastidious. For example, in a typical mitral valve surgery set-up with a known valve retractor system, two tissue retractors are generally mounted on a left chest retractor arm to retract cardiac tissue towards the left side of a patient. Another tissue retractor is mounted of an extension rod to retract cardiac tissue towards a patient's feet (see FIG. 18A). The extension rod is also mounted to the left chest retractor arm in a substantially perpendicular and generally horizontal orientation. If the surgeon wants to change the orientation of the tissue-engaging portion of the middle tissue retractor, for instance, the mounting clamp of the middle tissue retractor must be repositioned along the left chest retractor arm. Larger re-orientations generally require more translation of the mounting clamp along a chest retractor arm (or along a mounting rail substantially parallel to and slightly above a chest retractor arm). In certain cases, the re-orientation required is sufficiently great that the mounting clamp of the middle tissue retractor must be translated considerably along a chest retractor arm (or along its mounting rail) that it may interfere with the mounting clamp of an adjacent tissue retractor. This may lead to a major take down of the surgical set-up.

Some known tissue retractors are constructed with a number of rod-like extensions assembled in a rake-like arrangement to configure a tissue-engaging portion (see FIG. 18B). This may lead to concentrated loads exerted on an engaged cardiac tissue by the rod contact surfaces, and consequently be more prone to induce tissue trauma.

Some current retractor systems for valve surgery are comprised of a number of similar tissue retractors. These tissue retractors are generally of a fixed rigid geometry and design.

In some known retractor systems for valve surgery, the proximal shaft end of the tissue retractor must first be inserted and engaged within its mounting clamp before the tissue-engaging portion or blade may be placed into contact with the cardiac tissue. This may compromise the approach vector of a tissue retractor to a cardiac tissue desired to be retracted.

In minimally invasive valve surgery, the size of the surgical incision and the size of a retracted surgical window are considerably reduced. Vacuum-assisted venous drainage has been developed to reduce the size of venous cannulae used in cardiopulmonary bypass. The smaller sizes of these cannulae tend to prevent them from being an obstacle to the surgical procedure. However, the number of traction sutures and number of tissue retractors, either hand held or chest-retractor-mounted, still used in current approaches tends to be obstructive in certain cases, given the smaller surgical window.

Thus it is a first object of the present invention to provide a surgery tool tending to alleviate the above mentioned drawbacks.

It is another object of the present invention to aim to improve the exposure and access to the diseased cardiac valve by providing a valve surgery tool that tends to minimize the number of traction stay sutures, hand-held tissue retractors, or chest-retractor-mounted tissue retractors used in current valve surgery interventions.

BRIEF SUMMARY OF THE INVENTION

The invention provides a surgery tool comprising a finger arrangement adapted to displace tissue and provided with at least one finger movable with respect to at least one other finger, said tool comprising:
- two pivoting arms each comprising at least one finger provided at a free end portion thereof, said pivoting arms being movable between two positions; a first "closed configuration" in which said fingers are substantially close to each other; a second "deployed configuration" in which said fingers are substantially distant one from the other;
- a translating actuation member, movable along a translation axis and co-operating with at least one of said pivoting arms, whereby when said actuation member is actuated, said pivoting arms are pivotingly displaced.

The finger arrangement is variable in its configuration in order to suit or adapt to anatomic variations from patient to patient. The surgery tool also tends to minimize the number of traction sutures or hand held tissue retractors required in current surgical interventions.

It is advantageous to have a surgical apparatus whereby the orientation of the surgery tool relative to its position within the surgical window is independent of how the surgery tool is eventually secured to a chest retractor comprising said surgical apparatus.

Patient anatomy is variable and distinct. Surgical incisions are generally tailored and assume a variety of sizes and forms. Thus, it is advantageous to have a surgery tool with a tissue-engaging blade or finger design that tends to more evenly distribute the traction loads exerted on a cardiac tissue, and is more conform ant to the anatomical curvature of the cardiac tissue being retracted or to the unique surgical incision in cardiac tissue which is to be retracted. It is a further advantage to have a surgery tool, either hand held or chest-retractor-mounted, with adaptable finger arrangement whereby the radii and circumferential span formed by the tissue-engaging blades or fingers is adjustable to conform to the patient's distinct anatomy and to the unique nature of the surgical incision in the cardiac tissue.

It is also advantageous, especially in minimally invasive surgical approaches with small surgical windows, to have a single tissue retracting valve surgery tool, that is deployable and adjustable to a patient's specific anatomy tending to minimize or eliminate the number of traction sutures or tissue retractors used in current surgical interventions.

The surgery tool and associated surgical apparatus is advantageously capable of approaching a diseased valve from substantially any desired vector direction within the surgical window, and capable of securing the said valve surgery tool in any desired position and orientation relative to a cardiac tissue to be retracted, or any desired position and orientation relative to the flow axis through said diseased valve.

It is also advantageous to have a surgery tool and surgical apparatus that tends to facilitate in-process readjustment of the magnitude or direction of a tissue traction load applied by said surgery tool to a cardiac tissue, and this without a major tear-down of the surgical set-up.

It is also advantageous to have a surgical apparatus comprising a surgery tool that engages cardiac tissue with an adaptable finger arrangement, said surgery tool held by a positioning and articulation mechanism, said mechanism cooperating with a chest retractor, said surgical apparatus providing a substantially motionless, stable worksite in the vicinity of said engaged cardiac tissue.

It is also advantageous to have a surgery tool capable of first engaging cardiac tissue, then capable of being positioned and oriented in a desired manner relative to said cardiac tissue, and finally capable of being set in said desired position and orientation by being engaged in a positioning and articulation mechanism which cooperates with a chest retractor.

The translating actuation member is advantageously provided with a translating finger, whereby when said actuation member is actuated, said translating finger translates along a translation axis in substantially the same direction as the translating actuation member and said pivoting arms are pivotingly displaced between said first and second position.

The translating finger is adapted to move towards the pivoting fingers when said pivoting fingers are retracted towards said closed configuration, and away from the pivoting fingers when said pivoting fingers are deployed. In this way, all fingers substantially simultaneously contribute to reduce or enlarge the surgical worksite provided between the finger arrangement.

Various examples of the translating actuation member may be provided, such as a shaft, a cable (both of metallic or non-metallic materials), or other like translating actuation members.

In an advantageous example of a surgery tool, all fingers are movable with respect to each other.

The adjustment of said finger arrangement is preferably activated remotely from said fingers.

The surgery tool advantageously comprises a single actuator.

This enables, in use, for example during a valve surgery, while gently applying retraction to an incised aorta in the vector direction to best obtain exposure to the aortic valve, rotating the actuator knob of an aortic tissue retractor sufficiently to deploy said aortic tissue retractor to an open configuration whereby the resulting substantial radius of retraction formed through the deployed tissue-engaging blades or fingers of said aortic tissue retractor is substantially equivalent to the anatomic radius of said aorta.

The pivoting arms art preferably connected to a common pivoting axis disposed substantially along said translation axis, and are pivotingly actuated by two actuating linkages connected on one end to said actuation member and on the other end to said pivoting arms.

The actuator of the surgery tool co-operates with at least one of said pivoting arms in order to set said arms' respective positions. This position is in relation to a given position of the actuator.

The surgery tool of the invention is advantageously adapted for cardiac surgery, in particular valve surgery.

The invention also provides a surgery tool comprising a finger arrangement adapted to displace tissue and provided with at least one finger movable with respect to at least one other finger, said tool comprising:
- two pivoting arms each comprising at least one pivoting finger provided at a free end portion thereof, said pivoting arms being movable between two positions;
- a first "closed configuration" in which said pivoting fingers are in substantially close proximity one with respect to the other;
- a second "deployed configuration" in which said pivoting fingers are substantially distant one with respect to the other;
- a translating actuation member, movable along a translation axis and co-operating with said pivoting arms and provided with a translating finger, whereby when said actuation member is actuated, said translating finger translates along said translation axis in substantially the same direction as the translation member and said pivoting arms are pivotingly displaced between said first and second configuration.

In a preferred example of a surgery tool, all fingers are movable with respect to each other.

The adjustment of said finger arrangement is preferably activated remotely from said fingers.

The surgery tool of the invention preferably comprises a single actuator.

The pivoting arms are advantageously connected to a common pivoting axis disposed substantially along said translation axis and are pivotingly actuated by two actuating linkages connected on one end to said actuation member and on the other end to said pivoting arms.

The surgery tool of the invention is advantageously adapted for cardiac surgery, in particular valve surgery.

The invention also provides a surgery tool for cardiac surgery comprising a finger arrangement adapted to displace tissue and provided with at least one finger movable with respect to at least one other finger, said finger arrangement being adapted to provide between said fingers a surgical worksite and said fingers being movable between a first configuration in which said surgical worksite is minimal and a second configuration in which said surgical worksite is maximal.

The surgery tool is advantageously designed as a self-locking tool so that the pivoting arms may be locked in any intermediate position between said closed and deployed configurations. As such, the position of said fingers may also be fixed in any said locked intermediate position while said fingers are free to orient or pivot about said locked intermediate position and capable of assuming an ideal orientation for engagement with cardiac tissue.

Preferably, the surgery tool comprises:
a translating member movable along a translation axis,
a translating finger connected to said translating member,
two pivoting arms co-operating with said translating member,
a second and a third finger being connected to each pivoting arm,
whereby when said translating member is translated, said first finger translates along said translation axis in substantially the same direction as the translation member,
and said second and third fingers are pivoted about a common pivoting axis to move towards said translation axis or away from said translation axis in order to adapt the dimensions of said surgical worksite.

The surgery tool tends to provide adaptability to suit the specific patient's anatomy, tends to avoid the need for band held retractors kept in place by the surgical assistant, tends to permit in-process re-adjustment of the configuration of the surgery tool without disrupting the surgical set-up, attempts to provide a clean, less-encumbered surgical workspace. The surgery tool aims to provide the surgeon with the ability to approach and retract the desired cardiac tissue from any vector direction within the surgical workspace in particular, if engaged with a positioning and articulation mechanism which in turn cooperates with a chest retractor.

The surgery tool provides a surgical worksite that is variable and is preferably contained within a substantially circular area defined by the respective positions of said fingers.

The surgery tool of the invention is advantageously adapted for valve surgery.

The present invention also provides a valve surgery tool for performing valve surgery comprising three tissue-engaging blades, of which one of the said blades is capable of translating through a housing, while the other two blades are entrained to rotate in generally opposing directions around said housing by the action of this said first blade.

The first blade preferably translates through a housing by virtue of an actuator, said actuator entrains two actuating linkages to move and rotate in generally opposing directions relative to said housing, said actuating linkages each entrain one trailing linkage to rotate in a generally opposing direction to the other trailing linkage, said trailing linkages each entrain one tissue engaging blade to rotate relative to said housing in a generally opposite direction to the other tissue engaging blade.

In a preferred embodiment, the actuating linkages are pivotingly engaged to said actuator and to the said trailing linkages, and the said tissue-engaging blades are pivotingly engaged to the said trailing linkages.

The surgery tool is advantageously connected to a positioning means, said positioning means is capable of setting said valve surgery tool in virtually any substantially stable spatial position and orientation within a surgical workspace, said valve surgery tool being pivotally connected to a stable surgical platform via said positioning means.

These and other objects of the present invention will become apparent from the description of the present invention and its preferred embodiments which follows.

BRIEF DESCRIPTION OF THE DRAWINGS

For better understanding of the present invention and to show more clearly how it may be carried into effect, reference will now be made by way of illustration and not of limitation to the accompanying drawings, which show an apparatus according to the preferred embodiments of the present invention, and in which:

FIG. 6A is a top view of a valve surgery tool in the nature of an aortic tissue retractor in its closed, non-deployed configuration according to a first embodiment of the present invention;

FIG. 6B is a top view of a valve surgery tool in the nature of an aortic tissue retractor in its open, maximum deployed configuration according to a first embodiment of the present invention;

FIGS. 8A–8C illustrate the definition of an outer cardiac tissue engaging blade which forms a part of a valve surgery tool in the nature of an aortic tissue retractor according to a first embodiment of the present invention;

FIGS. 9A–9C illustrate the definition of a center cardiac tissue engaging blade which forms a part of a valve surgery tool in the nature of an aortic tissue retractor according to a first embodiment of the present invention;

FIG. 14A is a top view of a valve surgery tool id the nature of an atrial tissue retractor in its closed, non-deployed configuration according to a second embodiment of the present invention;

FIG. 14B is a top view of a valve surgery tool in the nature of an atrial tissue retractor in its open, maximum deployed configuration according to a second embodiment of the present invention;

FIGS. 15A–15C are right angle projection views of a valve surgery tool in the nature of an atrial tissue retractor according to a second embodiment of the present invention;

FIGS. 16A–16C illustrate the definition of a cardiac tissue engaging blade which forms a part of a valve surgery tool in the nature of an atrial tissue retractor according to a second embodiment of the present invention;

FIGS. 17A–17C illustrate an alternative definition of a cardiac tissue engaging blade which forms a part of a valve surgery tool in the nature of an atrial tissue retractor according to a second embodiment of the present invention;

DETAILED DESCRIPTION OF THE INVENTION

The features and principles of this invention can be applied, in whole or in part, to other types of valve surgery, cardiac surgery, or other surgery requiring the exposure of and access to an anatomical organ or like member generally contained within an organ chamber or major vessel that must be penetrated and retracted in order to create a surgical opening, or surgical worksite, through which to perform the surgical intervention on said anatomical organ or like member. The descriptions that follow will however be illustrated in the context of aortic and mitral valve surgery.

In part, the embodiments of this invention may be advantageously applied, if desired, to the chest retractor described in copending Canadian patent application Serial No. 2,216, 893 filed on Sep. 30, 1997 in the names of Cartier and Paolitto and entitled "Sternum Retractor for Performing Bypass Surgery on the Beating Heart" and in copending Canadian patent application Serial No. 2,237,877 filed on Jun. 26, 1998 in the names of Paolitto et al. and entitled "Chest Retractor for Performing Cardiac Surgery", for which a corresponding PCT application has been filed on Jun. 25, 1999 in the names of Paolitto et al. and entitled "Surgical Retractor Having Low-Friction Actuating Means and Contoured Blade Arms", the contents of which are incorporated herein by reference. In part, the embodiments of this invention may be advantageously applied, if desired, to the positioning means described in copending Canadian patent application Serial No. 2,216,893 filed on Sep. 30, 1997 in the names of Cartier and Paolitto and entitled "Sternum Retractor for Performing Bypass Surgery on the Beating Heart", the contents of which is incorporated herein by reference. Alternatively, the embodiments of the invention may also be applied to other types of chest retractors and other types of positioning means capable of securing the valve surgery tool according to the present invention in a substantially stable orientation and position relative to the chest retractor. Alternatively, the chest retractor may be replaced by other substantially stable surgical platforms that may co-operate with a positioning means to secure the valve surgery tool according to the present invention. Such surgical platforms would include: a surgical table, a surgical bridge or truss or truss member attached to a surgical table and spanning the patient or set adjacent to the patient, or other like platforms.

During the course of a cardiac valve surgery, a surgeon needs to perform certain tasks within a surgical workspace. This surgical workspace is defined by an area that contains the perimeter of a deployed chest retractor and a buffer zone therebeyond, and said area extending below to the depth of the patient's thorax, and above to the height above the retracted chest cavity in which the surgical apparatus comprising the valve surgery tool is contained and manipulated.

Figure 1:
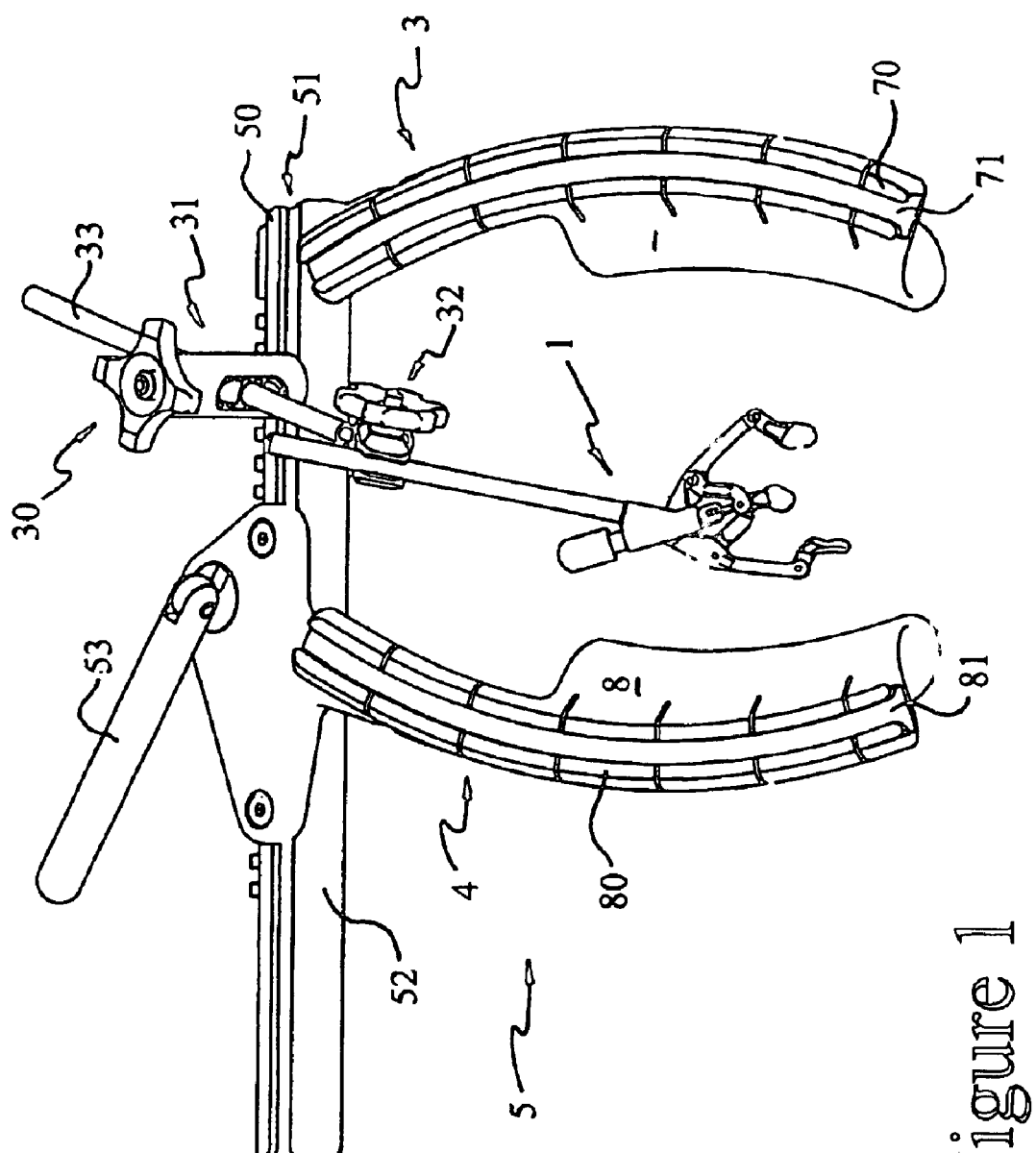
FIG. 1 is a perspective view of a surgical apparatus comprising a valve surgery tool according to a first embodiment of the present invention.
Figure 2:
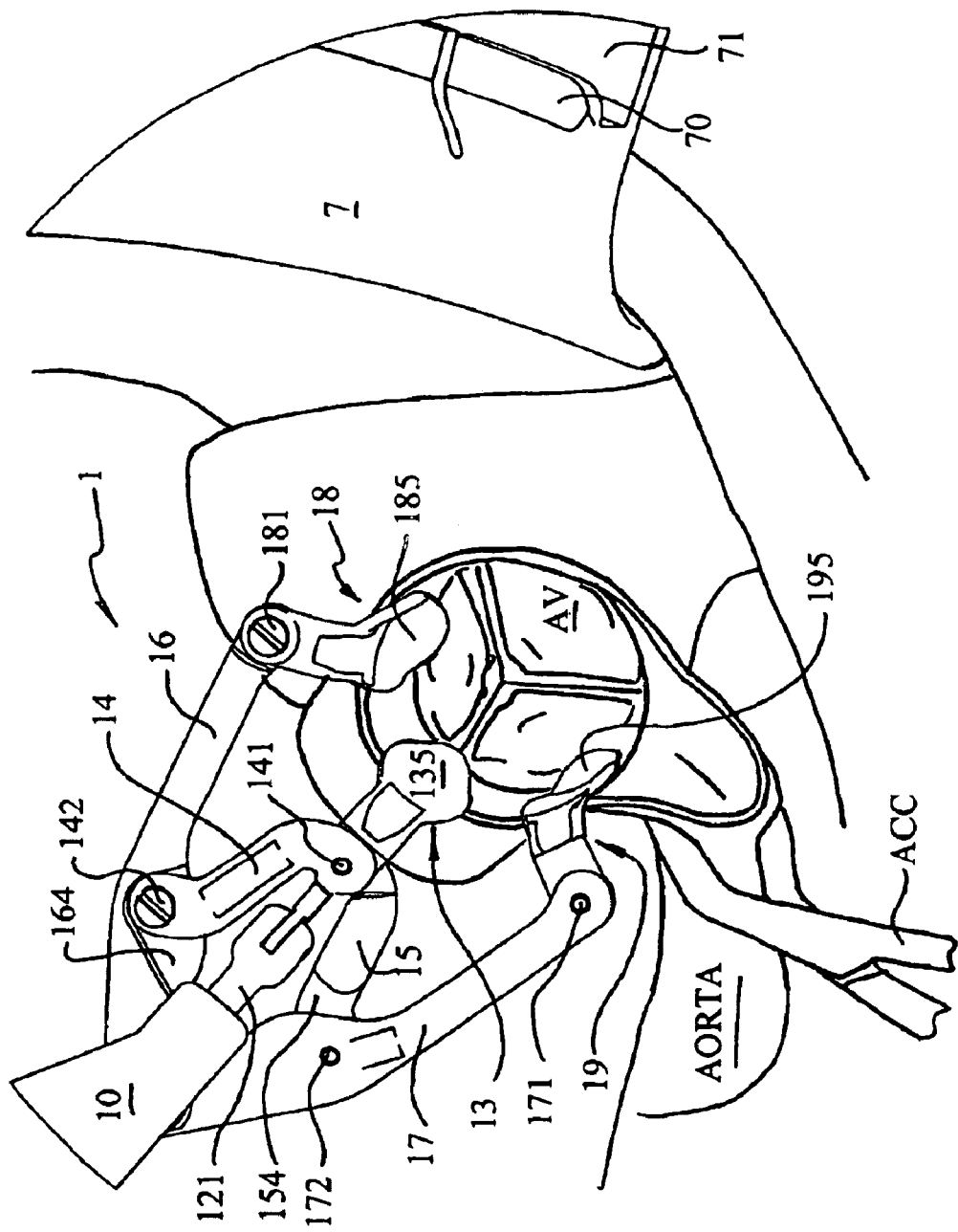
FIG. 2 is an enlarged top view of a deployed valve surgery tool in the nature of an aortic tissue retractor engaged with the cardiac tissue to expose the aortic valve according to a first embodiment of the present invention.

By way of a general overview and with reference to FIG. 1, a surgical apparatus with which the invention may be used is comprised of three main components, a valve surgery tool in the nature of an aortic tissue retractor 1, a positioning means such as positioning and articulation mechanism 30 and a chest retractor such as sternum retractor 5. The sternum retractor 5 is illustrated in its deployed state, thereby creating and maintaining the surgical window that provides the surgeon with access to the patient's internal cardiac tissue, which includes the pericardium, epicardium, myocardium, endocardium, tissue of the septal wall, aorta tissue, vena cava tissue, cardiac valves, heart muscle, the coronary arteries and veins, the pleurae, the thymus, and other like anatomical tissue.

The sternum retractor 5 includes four major parts: (i) an elongated rack bar 52, (ii) a first retractor spreader arm 3 being preferably fixed to the rack bar 52, (iii) a second retractor spreader arm 4 being preferably movable with respect to the rack bar 52, and (iv) an crank handle 53 for effecting movement of the retractor spreader arm 4 relative to retractor spreader arm 3.

Retractor spreader arms 3 and 4 extend in a direction substantially transversely with regard to rack bar 52, generally in the same direction therefrom and in a parallel orientation with respect to one another. The movable arm 4 can be displaced along the rack bar 52, and relative to the other arm 3, preferably through the rotation of the crank handle 53 activated by the surgeon. The crank handle 53 is operatively connected to rack bar 52 and to the other spreader arm 4, and is translatable along the length of the rack bar 52. This is preferably achieved by the engagement of a pinion mechanism (not shown) of crank handle 53 with the rack teeth on rack bar 52. Two retractor blades 7 and 8 are respectively provided with the retractor spreader arms 3 and 4, preferably disposed below the rack bar 52 when the sternum retractor 2 is deployed on a patient. The retractor blades 7 and 8 engage with and serve to retract a portion of the patient's incised skin, the two halves of the patient's incised sternum and the patient's ribcage thereby exposing the cardiac tissue to be operated on through the resultant surgical window. When viewing the resultant surgical window from above the patient, the retractor arms 3 and 4 of the deployed sternum retractor 5 each have a generally arcuate orientation.

The sternum retractor 5 advantageously comprises arcuate rails 70 and 80 along the top of arcuate retractor spreader arms 3 and 4, respectively. The rails 70 and 80 configure an inverted T-slot arcuate passage 71 and 81, respectively, preferably centrally located within said rails, and preferably extending throughout the entire arcuate length of said rails. A similar linear longitudinal rail 50, may also be configured along the top of rack bar 52. Longitudinal rail 50 is also configured with an inverted T-slot longitudinal passage 51, preferably extending throughout its entire longitudinal length. These said rails form a mounting perimeter that can advantageously serve to engage a positioning and articulation mechanism 30 that may be utilized to set a valve surgery tool 1 in virtually any substantially stable position and orientation within a surgical workspace. As well, these rails can also be utilized to engage other surgical apparatus, that may need to be secured along the perimeter of the sternum retractor 5 during cardiac valve surgery. Although FIG. 1 illustrates a sternum retractor 5, a smaller scaled-down version used in mini-sternotomy or thoracotomy incisions may also be used without departing from the spirit of the invention. In the embodiments that follow, the surgical apparatus is illustrated with the rack bar 52 of sternum retractor 5 placed towards the patient's feet.

As further illustrated in FIGS. 4–7, the first embodiment of a valve surgery tool in the nature of an aortic tissue retractor 1 according to the present invention is comprised mainly of a housing 10, an actuator 11, a translating actuating member in the nature of actuating piston 12, two actuating arms or linkages 14 and 15, two pivoting arms or trailing linkages 16 and 17, and three fingers or cardiac tissue engaging blades 13, 18, and 19.

Housing 10 is configured with a linear through-passage formed by guide hole 101 (FIG. 7B) and threaded bore 105, a blind threaded boss 103, and a blind boss fitting 107. Boss fitting 107 serves to engage second articulation rod 115. The male fitting 116 on the end of second articulation rod 115 is inserted into a bore 108 of boss fitting 107 and preferably permanently secured to the housing 10 by brazing, welding, or other like means. Alternatively, rod 115 may be mechanically assembled and demountably secured by virtue of a threaded interface between male fitting 116 and bore 108, or other like means. The longitudinal axis of the bore 108 (and consequently the longitudinal axis of the second articulation rod 115) forms an angle θ1 (preferably 35±5 degrees) with the longitudinal axis of the threaded bore 105 in housing 10, as will be defined in greater detail below. Second articulation rod 115 is preferably cylindrical so that it can rotate freely within the jaws of spherical clamp 32.

Figure 7B:
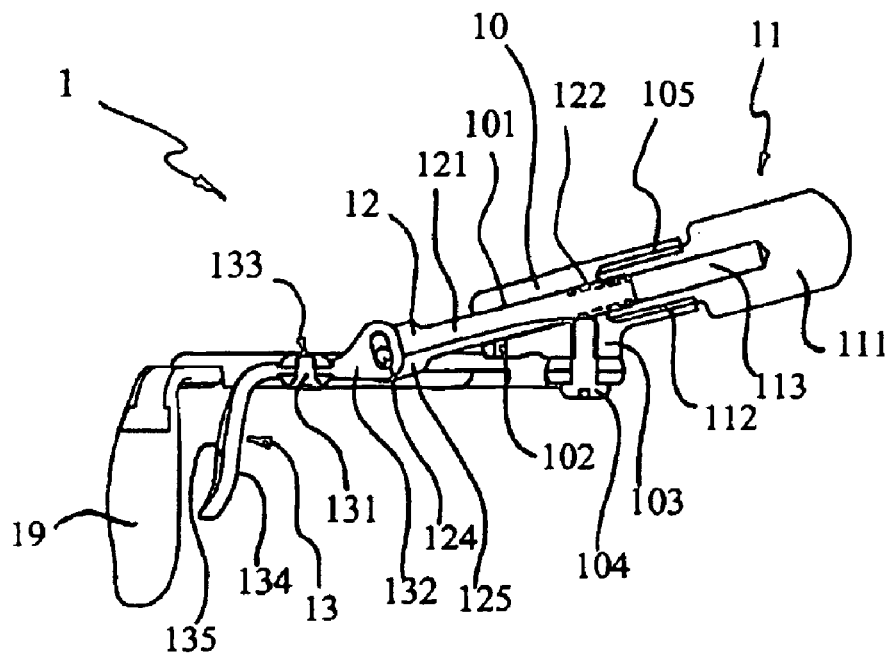
FIG. 7B is a section view through the valve surgery tool illustrated in FIG. 6B.

Housing 10 serves to contain actuator 11 and actuating piston 12. Actuator 11 is comprised of a knurled actuator knob 111 and a threaded shaft 112. A portion of the length of threaded shaft 112 and knurled knob 111 is drilled out and tapped along the centerline of said shaft 112 and knob 111 to configure an internally threaded bore 113 (FIG. 7B). The external thread on threaded shaft 112 mates with the internal thread on threaded bore 105 of the actuator housing 10. The thread between shaft 112 and bore 105 is preferably a fine pitch right hand thread. The internal thread on threaded bore 113 mates with thread 122 of actuating piston 12. Thread 122 is preferably a fine pitch left hand thread.

Actuating piston 12 is comprised of a clevis 123, a guide shaft 121, and an external thread 122. Clevis 123 serves to engage center blade 13 by installing retention pin 124 through the holes in the two flanges forming clevis 123 and through the elongated slot 136 in center blade 13. Guide shaft 121 serves to guide actuating piston 12 as it translates through the guide hole 101 in the housing 10. The centerline of hole 101 also defines a translation axis for actuating piston 12.

The first step in the mechanical assembly of the aortic tissue retractor 1 consists of fully threading shaft 112 of actuator 11 into threaded bore 105 of housing 10. The actuating piston 12 is then inserted into said housing from the opposite end, and the first two or three threads of external thread 122 screwed into the threaded bore 113 of actuator 11. At this point, the clevis end 123 is rotated slightly to align longitudinal anti-rotation slot 125 on the actuating piston 12 with hole 109 in housing 10. Anti-rotation pin 102 is then inserted into hole 109 such that the inserted end of the pin 102 (FIG. 7B) extends into guide hole 101 and engages with longitudinal slot 125. The pin 102 stays engaged with slot 125 throughout the range of translation of actuating piston 12 within housing 10.

The aortic tissue retractor 1 is deployed through the rotation of actuator knob 111. This rotation translates the actuator 11 relative to housing 10 by virtue of the threaded interface between actuator shaft 112 and threaded bore 105. The translation of actuator 11 entrains the translation of actuating piston 12, since the two said components are engaged by virtue of a threaded interface at thread 122 and 113. The rotation of actuator 11 relative to housing 10 does not entrain a rotation of actuating piston 12 since the engagement of anti-rotation pin 102 within longitudinal slot 125 prevents the rotation of actuating piston 12 relative to housing 10. By virtue of the two opposing threads (one right hand thread between housing 10 and actuator 11 and one left hand thread between actuator 11 and actuating piston 12), the translation of actuator knob 111 relative to housing 10 is amplified at clevis 123 relative to said housing. The effect of anti-rotation pin 102 causes the relative threading and unthreading between actuator 11 and actuator piston 12 when the actuator knob 111 is rotated. Conversely, the translation of clevis 123 relative to housing 10 may be reduced relative to the translation of actuator knob 111 relative to said housing, if the same thread type is used between both housing 10 and actuator 11 and actuating piston 12 and actuator 11 (i.e. both left hand threads or both right band threads). The ratio of the amplification or reduction of translation between actuator 11 and piston 12 may be tailored by selecting different thread pitches for each of the two threads.

The use of two cooperating threads as described above aims to minimize the diameter and overall size of the components that make up the aortic tissue retractor 1, while tending to maintain an effective translation of the actuating piston 12 and consequently an effective deployment of the aortic tissue retractor 1. Effective translation implies a generally small rotation of the actuating knob 111 produces a relatively greater translation of the actuating piston 12 and conversely a generally rapid deployment of the aortic valve surgery tool 1. Alternatively, the two cooperating threads may be replaced by a single coarser pitch thread. However, this would be at the expense of requiring thicker cylindrical shells for the housing 10 and shaft 112 in order to accommodate the coarser, deeper threads. Moreover, larger and less compact components for the aortic valve retractor 1 tend to be more obstructive when the said aortic valve retractor 1 is deployed within a surgical window. Alternatively, the cooperating thread design may be replaced by a multiple start thread between actuator 11 and housing 10 to tend to provide effective translation of actuating piston 12 with respect to housing 10.

Two actuating linkages 14 and 15 and two trailing linkages 16 and 17 cooperate as a linkage mechanism, or arrangement, whereby said actuating linkages 14 and 15 serve to transform the linear translation of actuating piston 12 into opposite angular rotations of trailing linkages 16 and 17 about threaded boss 103 on housing 10. In the embodiment of the aortic tissue retractor 1 as illustrated in FIGS. 1–7, the linkage mechanism is preferably configured to produce equal and opposite motions (mirror-image movement) of the two actuating linkages 14, 15 and equal and opposite motions of the trailing linkages 16, 17 relative to housing 10. Consequently, left actuating linkage 14 is identical to right actuating linkage 15 and left trailing linkage 16 is identical to right trailing linkage 17. This has the added advantage of commonizing component for the aortic tissue retractor 1.

Two flat faces 137 and 138, preferably disposed on a portion of center blade 13 between plate 132 and contact surface 134, act as bearing faces serving to guide the rotation of actuating linkages 14 and 15 about hole 133 through said flat faces. Actuating linkages 14 and 15 are substantially planar on one side forming a substantial s-shape in said plane. The s-shape configuration of the said actuating linkages tends to provide a compact arrangement of aortic tissue retractor 1 in its closed non-deployed position or configuration as illustrated in FIG. 6B. Left actuating linkage 14 is configured with two flat faces 144 and 145 at opposing free ends of said linkage. Faces 144 and 145 are offset parallel to the plane of the s-shape preferably to a depth of at least one half of the thickness of said actuating linkage 14. Face 145 will rotatingly mate with flat face 137 of center blade 13 once the assembly of the aortic tissue retractor 1 is complete. Similarly, right actuating linkage 15 is configured with two flat faces 154 and 155 at opposing free ends of said linkage. Faces 154 and 155 are offset parallel to the plane of the s-shape preferably to a depth of at least one half of the thickness of said actuating linkage 15. Face 155 will rotatingly mate with flat face 138 of center blade 13 once the assembly of the aortic tissue retractor 1 is complete.

Actuating linkages 14 and 15 are pivotingly engaged and may pivot freely about faces 137 and 138 respectively of center blade 13 by virtue of a pin-like mechanical joint. Countersink screw 131 is inserted into countersink hole 151 of actuating linkage 15, through hole 133 in center blade 13 and threaded into tapped hole 141 of actuating linkage 14. Screw 131 is threaded into tapped hole 141 sufficiently to create a slight gap between faces 145, 137, 138, and 155. This slight gap maintains said faces substantially parallel but free to rotate during the deployment of the aortic tissue retractor 1. Screw 131 is subsequently staked, brazed or welded thereby fixing it relative to actuating linkage 14. The shank of screw 131 thereby acts as a pin or axle which rotates relative to hole 133 in center blade 13 and hole 151 in actuating linkage 15. Once the mechanical joint assembly is complete, holes 133, 141, and 151 are aligned and represent the pivot axis of actuating linkages relative to center blade 13. Countersink screw 131 is used in order to create a flush surface along actuating linkage 15. This pin-like mechanical joint may also be produced by riveting or other like mechanical fastening means which allow the substantially free rotation of one linkage relative to the other.

The opposing free end of each of actuating linkages 14 and 15 are pivotingly engaged with trailing linkages 16 and 17, respectively. Trailing linkages 16 and 17 are substantially planar and are preferably configured with one bend (approximately 20 degrees) within said plane. Flat face 144 of left actuating linkage 14 is rotatingly engaged with flat face 164 of left trailing linkage 16, said faces 144, 164 helping to guide the rotation of left trailing linkage 16 relative to left actuating linkage 14. Flat face 164 is parallel to the plane defining the substantially planar configuration of left trailing linkage 16 and is created by a material cut-out in said linkage 16 at a location between the free ends of said linkage 16 preferably at the bend location. The bend in trailing linkages 16 and 17 tends to provide a compact arrangement of aortic tissue retractor 1 in its closed, non-deployed position or configuration as illustrated in FIG. 6A. Countersink screw 142 is inserted in countersink hole 143 of left actuating linkage 14 and threaded into tapped hole 162 (not shown). Screw 142 is threaded into tapped hole 162 sufficiently to create a slight gap between faces 144 and 164. This slight gap maintains said faces substantially parallel but free to rotate during the deployment of the aortic tissue retractor 1. Screw 142 is subsequently staked, brazed or welded thereby fixing it relative to left trailing linkage 16. The shank of screw 142 thereby acts as a pin or axle which rotates relative to hole 143 in left actuating linkage 14. Once the mechanical joint assembly is complete, holes 143 and 162 are aligned and represent the pivot axis of left actuating linkage 14 relative to left trailing linkage 16. Similarly, countersink screw 152 is inserted in countersink hole 153 of right actuating linkage 15 and threaded into tapped hole 172. Screw 152 is threaded into tapped hole 172 sufficiently to create a slight gap between faces 154 and 174. This slight gap maintains said faces substantially parallel but free to rotate during the deployment of the aortic tissue retractor 1. Screw 152 is subsequently staked, brazed or welded thereby fixing it relative to right trailing linkage 17. The shank of screw 152 thereby acts as a pin or axle which rotates relative to hole 153 in right actuating linkage 15. Once the mechanical joint assembly is complete, holes 153 and 172 are aligned and represent the pivot axis of right actuating linkage 15 relative to right trailing linkage 17.

Left trailing linkage 16 is configured with two other flat faces 165, 166 disposed at the opposing free ends of said linkage 16, both parallel to face 164 and to each other. Right trailing linkage 17 is configured with two other flat faces 175, 176 disposed at the opposing free ends of said linkage 17, both parallel to face 174 and to each other. One free end of each of trailing linkages 16 and 17 is pivotingly engaged with housing 10 at threaded boss 103, and free to pivot relative to said housing 10 and to the other trailing linkage. Pan head screw 104 is inserted through hole 163 in linkage 16, through hole 173 in linkage 17, and threaded into threaded boss 103 of housing 10. Flat face 166 is rotatingly engaged with flat face 176. Screw 104 is threaded into threaded boss 103 sufficiently to create a slight gap between faces 167, 166, 176, and 177. This slight gap maintains said faces substantially parallel but free to rotate during the deployment of the aortic tissue retractor 1. Screw 104 is subsequently staked, brazed or welded in threaded boss 103 thereby fixing it relative to housing 10. The shank of screw 104 thereby acts as a pin or axle which rotates relative to hole 163 in linkage 16 and hole 173 in linkage 17. Once the mechanical joint assembly is complete, holes 163, 173, and threaded hole in boss 103 are aligned and represent the common pivoting axis of trailing linkages 16 and 17 relative to housing 10.

The other free end of trailing linkage 16 is pivotingly engaged with left tissue-engaging blade 18. Countersink screw 181 is inserted through countersink hole 182 in blade 18 and threaded into tapped hole 161 of trailing linkage 16. Flat face 183 is rotatingly engaged with flat face 165. Screw 181 is threaded into tapped hole 161 sufficiently to create a slight gap between faces 183 and 165. This slight gap maintains said faces substantially parallel but free to rotate during the deployment of the aortic tissue retractor 1. Screw 181 is subsequently staked, brazed or welded in tapped hole 161 thereby fixing it relative to trailing linkage 16. The shank of screw 181 thereby acts as a pin or axle which rotates relative to hole 182 in left tissue-engaging blade 18. Once the mechanical joint assembly is complete, holes 183 and 161 are aligned and represent the pivot axis of left tissue-engaging blade 18 relative to trailing linkage 16.

Similarly, the other free end of trailing linkage 17 is pivotingly engaged with right tissue-engaging blade 19. Countersink screw 191 is inserted through countersink hole 192 in blade 19 and threaded into tapped hole 171 of trailing linkage 17. Flat face 193 is rotatingly engaged with flat face 175. Screw 191 is threaded into tapped hole 171 sufficiently to create a slight gap between faces 193 and 175. This slight gap maintains said faces substantially parallel but free to rotate during the deployment of the aortic tissue retractor 1. Screw 191 is subsequently staked or brazed in tapped hole 171 thereby fixing it relative to trailing linkage 17. The shank of screw 191 thereby acts as a pin or axle which rotates relative to hole 192 in right tissue-engaging blade 19. Once the mechanical joint assembly is complete, holes 193 and 171 are aligned and represent the pivot axis of right tissue-engaging blade 19 relative to trailing linkage 17.

Figure 4:
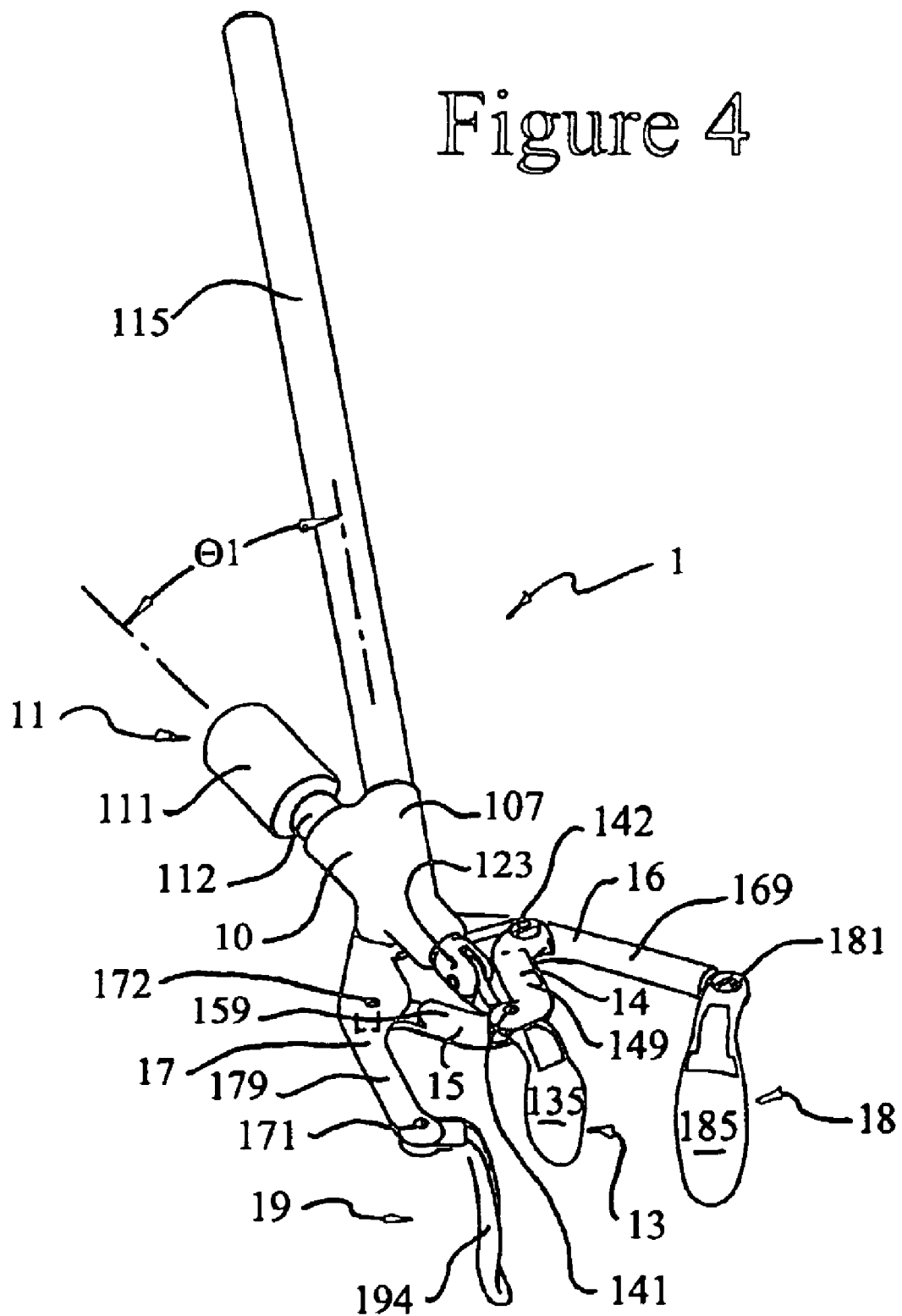
FIG. 4 is an isometric perspective view of a valve surgery tool in the nature of an aortic tissue retractor according to a first embodiment of the present invention.
Figure 5:
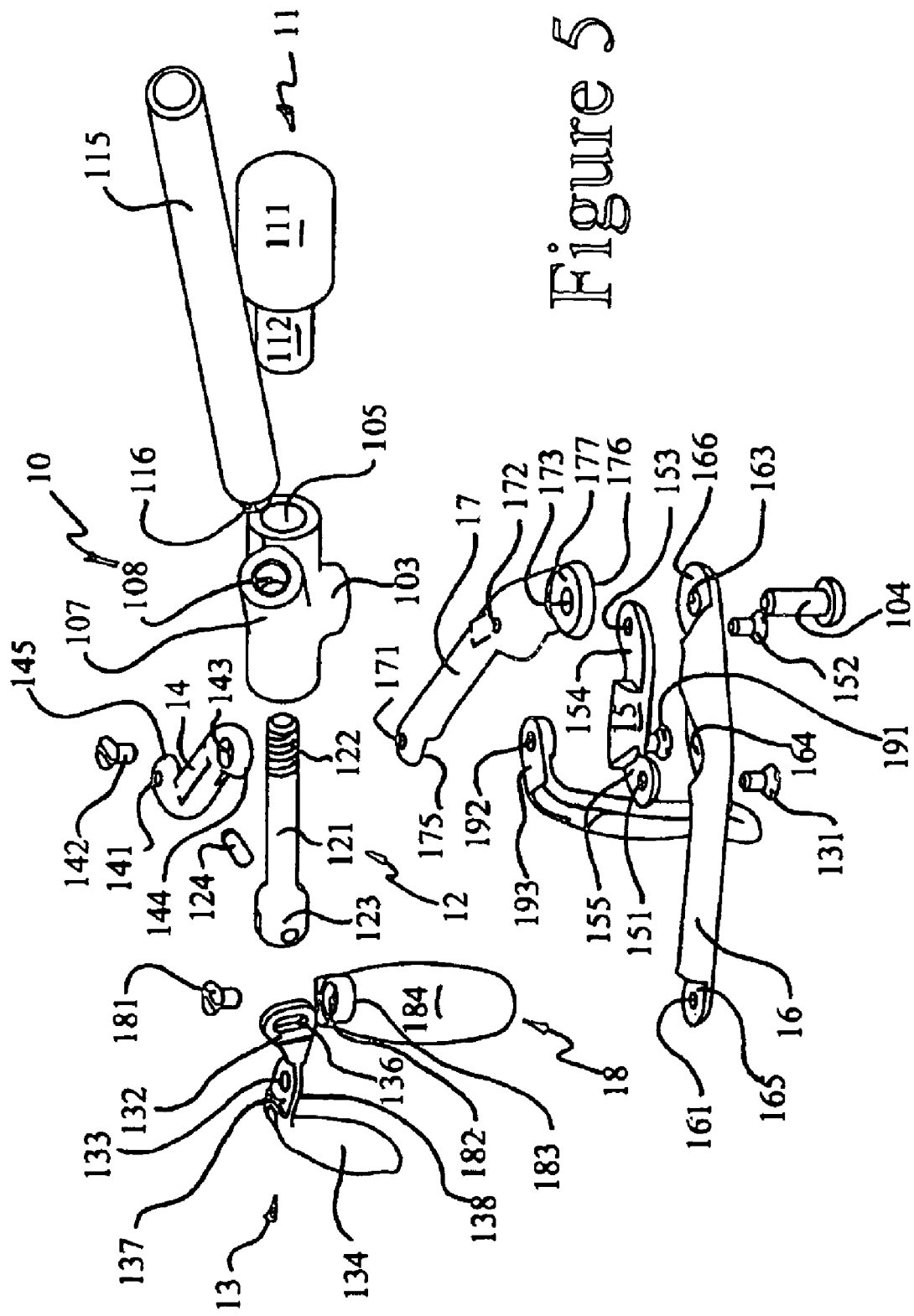
FIG. 5 is an exploded view of a valve surgery tool in the nature of an aortic tissue retractor according to a first embodiment of the present invention.
Figure 7A:
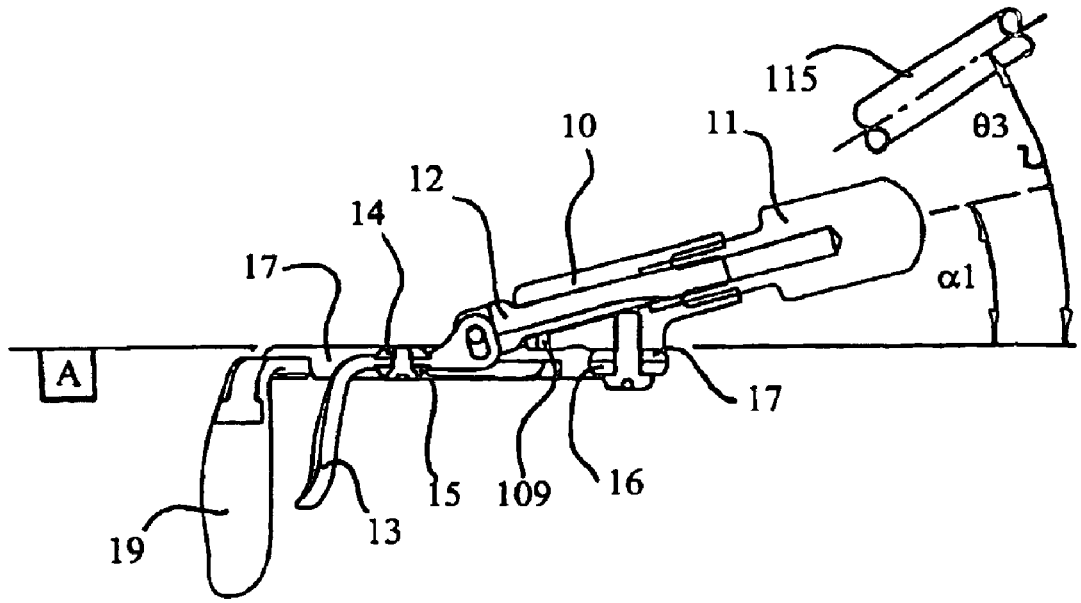
FIG. 7A is a section view through the valve surgery tool illustrated in FIG. 6A.

Once the aortic tissue retractor 1 is fully assembled, the top surfaces 149, 159, 169, 179 of linkages 14, 15, 16, and 17 respectively are contained in and define a plane A (FIGS. 4, 7A).

When not engaged with cardiac tissue, blades 18 and 19 of a fully assembled aortic tissue retractor 1 are free to pivot about their respective pivot axis. Relative to the longitudinal axis of their respective trailing linkage, these blades are free to pivot and assume an angle $\beta$ generally between 90 and −90 degrees (FIG. 6B). The longitudinal axis of trailing linkage 16 is defined as a line contained in plane A generally connecting tapped holes 161 and 162 on said linkage 16. The longitudinal axis is normal to each of the centerlines of said holes 161 and 162. The longitudinal axis for trailing linkage 17 is similarly defined. In FIG. 6B, blades 18 and 19 are shown in a pivot orientation (i.e. angle $\beta2$) which they would generally assume if engaged with the aortic tissue of an incised aorta of anatomic radius close to R2. As such, in this particular deployed configuration, blades 18 and 19 assume a substantial radius of retraction R2 and provide a surgical worksite that may be varied through a surgeon input applied at actuator 11, but in this particular instance said worksite is contained within a substantial circular area defined by said radius R2. In FIG. 6A, blades 18 and 19 are illustrated in a free state of pivot orientation where they assume an arbitrary angle $\beta1'$. In the closed, non-deployed configuration of the aortic tissue retractor 1, blades 18 and 19 may be pivoted in such a manner that a portion of their lateral edge comes into contact with non-contact surface 135 of center blade 13. In this pivot orientation, the three blades 13, 18 and 19 assume their most compact arrangement and are contained within a substantially circular area defined by a radius of retraction R=R1. At this limit condition, the pivot orientation of blade 18 and 19 is defined by angle $\beta1$ (not shown).

Faces 164 and 165 in trailing linkage 16; faces 174 and 175 in trailing linkage 17; faces 154 and 155 in actuating linkage 15; and faces 144 and 145 in actuating linkage 14 are offset parallel to plane A which generally contains their bent shape or s-shape. This aims to create a clean substantially planar surface along the tops of these said linkages, substantially free from any protrusion or depression when the aortic tissue retractor 1 is completely assembled. Consequently, this tends to minimize the likelihood of suture lines used to secure a replacement valve, for instance, from being entangled in any protrusion or depression that may otherwise exist as a result of joining linkages without these said offset faces. Countersink holes and countersink screws are preferably used in the assembly of actuating linkages, trailing linkages and tissue engaging blades to help create this said clean surface.

The spreading apart of actuating linkages and trailing linkages, along with the spreading apart of blades 18 and 19 occurs in directions parallel to plane A, throughout the entire range of deployed positions the aortic tissue retractor 1 is capable of assuming. The rotations of actuating linkages and trailing linkages about their respective pivot axes occur in a plane parallel to plane A. The translation of center blade 13 also occurs in a direction parallel to plane A.

The actuating piston 12 translates along an axis forming an angle $\alpha1$ with plane A, as illustrated in FIG. 7B. Consequently, slot 136 in center blade 13 is elongated to allow pin 124 engaged in clevis 123 of actuating piston 12 to translate within slot 136. Center blade 13 is slidingly engaged to actuating piston 12 through clevis 123. As aortic tissue retractor 1 is deployed, centerblade 13 translates along a translation axis that is substantially in the same direction as translation of actuating piston 12.

The closed, non-deployed configuration and the open, maximum deployed configuration of the aortic tissue retractor 1 are defined with reference to FIGS. 6A and 6B, respectively.

To facilitate insertion of aortic tissue retractor 1, even in small aortotomy incisions, the tissue-engaging blades 13, 18, 19 are capable of assuming a generally compact arrangement with a relatively small substantially circular radius of retraction R=R1 and a relatively small circumference of retraction C=C1 spanning through said blades in the closed, non-deployed configuration. The angle between trailing linkages 16, 17 in this generally compact arrangement is $\phi1$, and the pivot orientation of blades 18, 19 when substantially engaged with cardiac tissue is $\beta1$. Through the rotation of the actuation knob 111, and the resultant translation of actuating piston 12 and center blade 13, trailing linkages 16, 17 and actuating linkages 14, 15 rotate apart and provide a substantially continuous range of variable R, C, $\beta$, and $\phi$ up until the maximum deployed position or configuration of aortic tissue retractor 1 defined by R2, C2, $\beta2$, and $\phi2$. The maximum deployed configuration is designed to attempt to cater for the maximum size aorta generally encountered during aortic valve surgery. In between these two limit configurations, that is, the closed non-deployed and maximum deployed positions, the aortic tissue retractor 1 may be selectively adapted to attempt to cater to the entire spectrum of different size aortas encountered during aortic valve surgery as a function of patient variability. This tends to allow the aortic tissue retractor to be adapted to whatever specific patient anatomy the surgeon is presented with, thereby also tending to improve surgical access to the diseased valve.

The tissue contacting surface 184 of blade 18 is generally offset in a symmetric fashion away from the centerline of hole 182 and its pivot axis through said hole (FIG. 8C). The extending most point away from hole 182, identified as point X on the non-contact face 185 of blade 18 is at a distance d1 from the centerline of hole 182. This offsetting of tissue contacting surface 184 from the pivot axis of blade 18 tends to provide a more gradual and substantially continuous range of variable intermediate positions or settings defined by R, C, β, and φ as the surgeon deploys aortic tissue retractor 1 from its closed configuration when R=R1 to its open configuration when R=R2. Blade 19 is defined by preferably identical offsets relative to its pivot axis and hole 192. By virtue of this said offset, blades 18 and 19 also provide a linkage-like pivoting action during the deployment of the aortic tissue retractor 1.

In a specific example of an aortic tissue retractor the definition of the variables at the non-deployed closed configuration and corresponding maximum open configuration is as follows: R1=0.375 in., R2=0.875 in., C1=1.0 in., C2=1.525 in, φ1=15 degrees, φ2=45 degrees, β1=85 degrees (if blades 18 and 19 are pivoted about their pivot axis until they come into contact with blade 13 in the closed, non-deployed configuration), β2=72.5 degrees, d1=0.395 in., d2=0.64 in., d3=1.0 in., and d4=1.59 in. These values are approximate.

The desired retraction load and vector direction for the application of said retraction load on the engaged cardiac tissue is maintained by securing the aortic tissue retractor 1 to sternum retractor 5 through positioning and articulation mechanism 30. The positioning and articulation mechanism 30 allows the aortic tissue retractor 1 to be set in virtually any substantially stable position within the surgical workspace and relative to sternum retractor 5, with the plane A of the aortic valve tool 1 capable of being placed in virtually any orientation relative to the desired position within said surgical workspace. This tends to allow the surgeon to apply the desired retraction load on the engaged cardiac tissue in any vector direction within the surgical workspace and with the desired magnitude of retraction load.

The positioning and articulation mechanism 30 is preferably comprised of a first articulation member in the nature of a cylindrical post 31 and second articulation member in the nature of a spherical clamp 32, each capable of providing a multitude of motion degrees of freedom. Second articulation rod 115 of aortic tissue retractor 1 is inserted in between the clamping members of spherical clamp 32. The clamping members may engage articulation rod 115 anywhere along its longitudinal length. Final adjustments to the cardiac tissue retraction load may also occur with the articulation rod 115 engaged between clamping members of spherical clamp 32 before the entire positioning and articulation mechanism 30 assembly is rigidly secured through the action of each of the tensioning knobs of spherical clamp 32 and cylindrical post 31. In-process readjustments to the cardiac tissue retraction load may also occur by loosening one or both of each said tensioning knobs; and not disengaging the aortic tissue retractor 1 from the spherical clamp 32. With the tensioning knob of spherical clamp 32 slightly loosened, the aortic tissue retractor 1 is free to translate through the clamping members of spherical clamp 32, rotate about the axis of articulation rod 115, pivot about axis of first articulation rod 33, and articulate angularly within a plane formed by the centerlines of articulation rod 33 and articulation rod 115. With the tensioning knob of cylindrical post 31 loosened, articulation rod 33 is free to rotate about its longitudinal axis, is free to translate through the cylindrical post 31 in a direction along its longitudinal axis, is free to articulate into and out of the retracted chest cavity by increasing or decreasing the angle between its longitudinal axis and the centerline axis of cylindrical post 31, is free to rotate about the centerline axis of cylindrical post 31, and is free to slide within arcuate passage 81 (or 71 or 51). These motion degrees of freedom provide the mechanical flexibility to tailor the surgical set-up to distinct patient anatomies tending to result in an ergonomic deployment of the aortic tissue retractor 1. Cylindrical post 31 is preferably already installed with the first articulation rod 33 on the perimeter rail 50 (or 70 or 80) of sternum retractor 5 prior to engaging the cardiac tissue (incised aorta) with the aortic tissue retractor 1.

The open-ended jaw design of the spherical clamp 32 advantageously allows the aortic tissue retractor 1 to be engaged with the cardiac tissue prior to engaging its articulation rod 115 within the jaws of spherical clamp 32.

With the aortic tissue retractor 1 secured relative to the sternum retractor 5 by positioning and articulation mechanism 30, and with the cardiac tissue engaged by the blades 13, 18, 19 of the aortic tissue retractor 1, the actuator 11 provides the flexibility to re-adjust the retraction radius R and circumference of retraction C while said blades remain engaged with cardiac tissue and without disrupting the surgical set-up provided by positioning and articulation mechanism 30 and co-operating sternum retractor 5.

Figure 3:
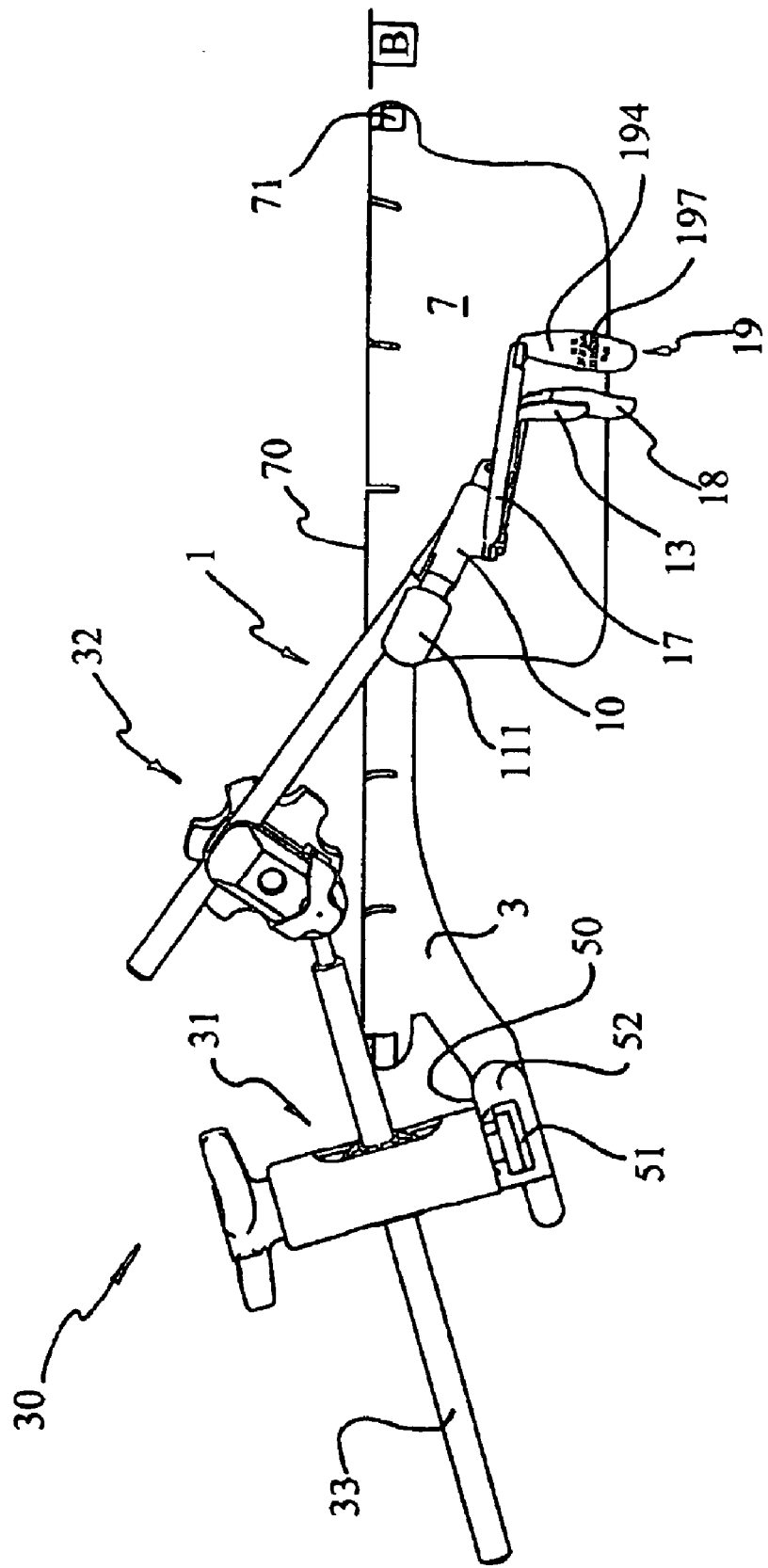
FIG. 3 is a side elevational view of a surgical apparatus comprising a valve surgery tool in the nature of an aortic tissue retractor according to a first embodiment of the present invention.

As illustrated in FIG. 3, often times during valve surgery the portion of the aortic tissue retractor 1 contained in plane A must be placed below a plane B defined by the arcuate rails 70 and 80 of retractor arm 3 and 4 respectively, of the deployed sternum retractor 5. Consequently, the aortic tissue retractor 1 is defined with an angle θ1 between the longitudinal axis of articulation rod 115 and the common translation axis through actuator 11 and actuating piston 12. The aortic tissue retractor 1 is defined with an angle θ2 between the longitudinal axis of articulation rod 115 and section plane 7A—7A, which is perpendicular to plane A and contains the centerline and translation axis of the actuating piston 12. The longitudinal axis of articulation rod 115 also forms an angle θ3 with plane A. These said angles tend to maintain the proximal end of articulation rod 115 more easily exposed to be held by spherical clamp 32. These said angles also tend to place the articulation rod 115 extending outward from the retracted chest cavity, in a vector direction less prone to interfere with blades 7 and 8 and arms 3 and 4 of sternum retractor 5 when aortic tissue retractor 1 is engaged with aorta tissue in the desired position and orientation of plane A during a typical aortic valve surgery.

The geometric definitions of the cardiac tissue contacting blades 13, 18, and 19 aim to minimize cardiac tissue trauma and cardiac tissue tearing during a valve surgery. The center blade 13 is preferably configured to be shorter in length L4 relative to the left and right blades 18 and 19. This is desirable in order to reduce the likelihood of interference or contact between the center blade 13 and a valve commissure, especially in a tri-leaflet valve intervention. The outer blades 18 and 19 are generally aligned between two adjacent valve commissures in a typical deployment of the aortic tissue retractor 1 during a tri-leaflet valve surgery and are preferably longer in length L1. Blades 18 and 19 are preferably of the same common blade definition. Alternatively, other designs are possible with all three blades configured with a common length L1, L4 or any other appropriate length.

Length L1 and width W1 of blade 18 and 19, length L4 and width W2 of blade 13, and the resulting circumference of retraction C obtained from the deployment of the aortic tissue retractor 1, to a suitable intermediate deployed position or setting, serve to support the circumference of an incised aorta during cardiac tissue retraction, tending to avoid the collapse of the incised aorta's curvature and circumference which may then hinder the surgeon's vision or access to the diseased aortic valve (labelled AV). The specific definition of the blades 13, 18, and 19 aim to distribute the cardiac tissue retraction loads over a greater tissue surface thereby tending to minimize the concentrated loads on cardiac tissue which is more likely to induce trauma and tearing as may be the case with traction stay sutures.

The extending-most point of blade 13 and blades 18, 19 relative to their respective pivot axis are identified as points Y and X, respectively, and are bent away from the contacting surfaces 134, 184, and 194 tending to avoid concentrated loads from being exerted on cardiac tissue during the insertion of aortic tissue retractor 1 into an aortotomy incision and during subsequent retraction of said incision. This also tends to avoid the likelihood of piercing cardiac tissue with the extending most portions of blades 13, 18, and 19.

FIG. 8A illustrates the blade definition for blade 18 (and by similarity also blade 19). Blade 18 extends below plane A in a substantially normal orientation to said plane A. The extending-most point X is offset a distance L1 below plane A and distance d1 away from the centerline defining hole 182. Section plane 8B—8B located a distance L3 above point X provides a cross-section parallel to plane A as illustrated in FIG. 8B. The radius of curvature of non-contact surface 185 in this cross-sectional plane is identified as r3. A section plane 8C—8C through the mid-span width of blade 18 provides a cross-sectional view through said blade 18, where said section 8C—8C is perpendicular to plane A. The non-contact surface 185 of blade 18 is preferably generated by defining a cross-sectional profile in section plane 8C—8C, and revolving said cross-sectional profile about an axis of revolution AR1 as illustrated in FIG. 8C. The contact surface 184 is defined by offsetting the resulting non-contact surface 185 by a distance equal to the blade 18 thickness. This offset need not be a parallel offset if the blade 18 is of variable thickness.

The cross-sectional profile in section plane 8C—8C of the non-contact surface 185 of blade 18 is substantially s-shaped and generally defined by three radii r4, r5, and r6. The inflection in this said profile (from convex close to plane A to concave close to point X) results in an inflected shape on the contact surface 184 (concave close to plane A to convex close to point X) which helps to maintain or support cardiac tissue engaged during tissue retraction. Moreover, the revolution of this inflected contact profile about axis AR1 tends to avoid sharp edges along the lateral edges of the blade 18. The width of blade 18 is the resultant distance between lateral edges of said blade, said lateral edges defined by r2 and r1 in FIG. 8A. The maximum blade width is W1.

FIG. 9A illustrates the blade definition for blade 13. Blade 13 extends below plane A in a substantially normal orientation to said plane A. The extending-most point Y is offset a distance L4 below plane C and distance d5 away from the centerline defining hole 133. Plane C is parallel to plane A and lies slightly below plane A. Section plane 9B—9B located a distance L6 above point Y provides a cross-section parallel to plane A and C as illustrated in FIG. 9B. The radius of curvature of non-contact surface 135 in this cross-sectional plane is identified as r9. A section plane 9C—9C through the mid-span width of blade 13 provides a cross-sectional view through said blade 13, where said section 9C—9C is perpendicular to plane A. The non-contact surface 135 of blade 13 is preferably generated by defining a cross-sectional profile in section plane 9C—9C, and revolving said cross-sectional profile about an axis of revolution AR2 as illustrated in FIG. 9C. The contact surface 134 is defined by offsetting the resulting non-contact surface 135 by a distance equal to the blade 13 thickness. This offset need not be a parallel offset if the blade 13 is of variable thickness.

The cross-sectional profile in section plane 9C—9C of the non-contact surface 135 of blade 13 is substantially s-shaped and generally defined by three radii r10, r11, and r12. The inflection in this said profile (from convex close to plane C to concave close to point Y) results in an inflected shape on the contact surface 134 (concave close to plane C to convex close to point Y) which helps to maintain or support cardiac tissue engaged during tissue retraction. Moreover, the revolution of this inflected contact profile about axis AR2 tends to avoid sharp edges along the lateral edges of the blade 13. The width of blade 13 is the resultant distance between lateral edges of said blade, said lateral edges defined by r7 and r8 in FIG. 9A. The maximum width of blade 13 is W2.

In a specific example of an aortic tissue retractor the definition of the tissue engaging blades 13, 18 and 19 is as follows: L1=0.975 in., L2=0.105 in., L3=0.210 in., L4=0.600 in., L5=0.115 in., L6=0.210 in., W1=0.320 in., W2=0.320 in., r1=0.250 in., r2=1.371 in., r3=0.375 in., r4=0.150 in., r5=1.840 in., r6=0.250 in., r7=0.230 in., r8=0.397 in., r9=0.375 in., r10=0.150 in., r11=1.840 in., r12=0.250 in., d1=0.395 in., d5=0.395 in. These values are approximate.

The aortic tissue retractor 1 is preferably configured with substantially smooth contact surfaces 134, 184, 194 since blades 13, 18, and 19 preferably mate with the inner lumen of an aorta. However, non-traumatic texturing may also be provided in the nature of smooth gradual ridges, depressions, dimples or other like features disposed on at least a portion of contact surface 134, 184, or 194 to attempt to enhance the adherence of the engaged cardiac tissue to the blades of the aortic tissue retractor 1. This non-traumatic texture is schematically represented in FIG. 3 as feature 197 on a portion of contact surface 194 of blade 19. Alternatively, said non-traumatic texture may also be comprised of a biocompatible hydrogel coating or biocompatible friction-enhancing polymer or elastomer.

The design of aortic tissue retractor 1 having blades 18 and 19 pivotingly engaged to trailing linkages 16 and 17 respectively, tends to allow the cardiac tissue retraction load to always be applied substantially normal to the engaged surface of the cardiac tissue being retracted, regardless of the angle φ between trailing linkages 16 and 17. As the aortic tissue retractor 1 is deployed from its closed configuration to its open configuration, the circumference of retraction C spanning between outer blades 18 and 19 increases and the resulting substantially circular radius of retraction R linking, or containing therein, all three blades also increases until a suitable R is obtained which conforms to the equivalent anatomic radius of the aorta. At this point, the cardiac tissue retraction load applied to the incised aorta by each of the said blades is substantially normal to the cardiac tissue engaged with each of said blades. This is achieved by having blades 18, 19 pivotingly engaged about the free end of their respective trailing linkages (16, 17), or pivoting arms, and capable of assuming a suitable pivot orientation or β angle relative to the cardiac tissue from the complete range of β angles available, as previously described. The equivalent anatomic radius is defined as the radius a flexible aorta may take if its anatomic circumference was reconfigured into a substantially perfect circle. In cases where the aorta is not flexible, the pivotingly engaged blades allow the contact surfaces 184 and 194 to independently reorient themselves such that they locally conform to the curvature of the non-flexible aorta. In this case the angle β for each blade 18 and 19 may not be equal, and a substantially noncircular spline may link all three tissue-engaging blades 13, 18, and 19 instead of a substantially circular radius of retraction R.

Alternatively, an aortic tissue retractor may also be configured with a center blade pivotingly engaged to a portion of the said linkage mechanism.

Translation of center blade 13 with respect to housing 10 is an important factor in attempting to produce a substantially linear relationship between the actuation input (rotation of knob 111 of actuator 11 in this first embodiment) and the resulting change in angle φ between trailing linkages 16 and 17. That is, for a given rotation of actuation knob 111, a substantially constant change in φ and change in radius of retraction R is obtained throughout the range of angles from φ1 to φ2 and corresponding range of radii from R1 to R2. Without the translation of the center blade 13, a given rotation of actuation knob 111 tends to produce a larger change in angle φ and larger change in radius R, as the aortic tissue retractor is deployed from its closed configuration to its maximum open configuration. In this first embodiment, the surgeon input is advantageously applied to aortic tissue retractor 1 through a single actuator 11, or more specifically through a rotation of actuator knob 111.

In broad terms, a surgical procedure for the set-up of a surgical apparatus with which the aortic tissue retractor 1 may be used during an aortic valve surgery, and relating to the present invention, preferably consists of:

(a) Performing a partial or midline sternotomy incision;
(b) Cauterizing any bleeding vessels subsequent to the sternotomy incision;
(c) Retracting the patient's ribcage through the deployment of sternum retractor 5;
(d) Placing the patient on cardiopulmonary bypass through the cross-clamping of the aorta and the installation of a series of cannulae to obtain aortic cannulation, right atrial cannulation and cannulation to administer cardioplegia;
(e) Making an oblique incision (aortotomy) around a portion of the aorta's circumference in the length of aorta between the diseased aortic valve and the aortic cross clamp (identified as ACC in FIG. 2);
(f) Installing cylindrical post 31 of positioning and articulation mechanism 30 on sternum retractor 5 at an approximate location along perimeter rails (50, 70, or 80) suitable for the patient's specific anatomy and surgeon work preference, typically along rack bar 52 of sternum retractor 5;
(g) While holding the aortic tissue retractor 1 by the second articulation rod 115, inserting the cardiac tissue engaging blades 13, 18, 19 in their closed configuration into the aortotomy incision and engaging the contact surfaces 134, 184, 194 of said blades along the internal circumference of the incised aorta between the incision and the diseased valve;
(h) While gently applying retraction in the vector direction to best obtain exposure to the aortic valve, rotating actuator knob 111 sufficiently to deploy the aortic tissue retractor 1 to a suitable open position whereby the substantial radius of retraction R formed through the deployed tissue engaging blades 13, 18, 19 is substantially equivalent to the anatomic radius of the aorta (creating the surgical worksite);
(i) Engaging the proximal end of second articulation rod 115 into the open ended spherical clamp 32 while gently maintaining the magnitude of the retraction load and the direction vector of the retraction load on the aortic tissue retractor 1;
(j) Slow and alternate tightening of each of the tensioning knobs of the cylindrical post 31 and spherical clamp 32 of the positioning and articulation mechanism 30 until the surgical setup is secured and fixed;
(k) If required, readjustment of the aortic tissue retractor 1 for more or less spreading of trailing linkages 16 and 17 and of blades 18 and 19, through rotation of actuating knob 111 (re-adjustment of radius of retraction R, circumference of retraction C, and surgical worksite);
(l) If required, readjustment of the magnitude of retraction load or the vector direction of retraction load through the loosening of tensioning knobs of the cylindrical post 31, spherical clamp 32, or both followed by a readjustment of the arrangement of the positioning and articulation mechanism 30;
(m) Performing the aortic valve surgical intervention;
(n) Once the intervention has been completed, rotating the actuator knob 111 to return the blades 13, 18, 19 of the aortic tissue retractor 1 towards their closed position;
(o) Loosening tensioning knob of the spherical clamp 32 and disengaging the aortic tissue retractor 1 from said spherical clamp of the positioning and articulation mechanism 30;
(p) gently retrieving the aortic tissue retractor 1 from the incised aortic incision;
(q) closing the aortotomy incision;
(r) taking the patient off cardiopulmonary assistance;
(s) closing retractor arms 3 and 4 and retrieving sternum retractor 5;
(t) closing the partial or midline sternotomy incision.

Alternatively, the aortic tissue retractor 1 may first be engaged within the jaws of spherical clamp 32 prior to engaging the cardiac tissue. Then, with the tensioning knobs of the spherical clamp 32 and cylindrical post 31 sufficiently loose to allow the free exploitation of all the motion degrees of freedom of the positioning and articulation mechanism 30, approach and subsequently engage the cardiac tissue with the blades 13, 18, 19 of the aortic tissue retractor 1. The remainder of the surgical procedure then follows steps (g), (h) and (J) to (u) as described above.

As described in the foregoing description, the aortic tissue retractor 1 tends to provide adaptability to suit the specific patient's anatomy, tends to avoid the need for hand held retractors kept in place by the surgical assistant, tends to permit in-process re-adjustment of the configuration of the aortic tissue retractor without disrupting surgical set-up, attempts to provide a clean, less-encumbered surgical workspace, and aims to provide the surgeon with the ability to approach and retract the desired cardiac tissue from any vector direction within the surgical workspace.

Alternatively to the aortic tissue retractor 1 described above, an aortic tissue retractor with different left and right actuating linkages and different left and right trailing linkages, and consequently different pivot points along these said linkages, may be configured to produce an aortic tissue retractor with unequal, skewed motion (not mirror-like) about the housing 10 of one actuating linkage relative to the other or one trailing linkage relative to the other.

Those skilled in the art may appreciate that the distances between the pivot axes on the trailing linkages and the actuating linkages, and the distance between the blade contacting surfaces and their respective pivot axes, may be modified from the configurations illustrated in order to achieve different ratios of R1 to R2, C1 to C2, φ1 to φ2, and β1 to β2 defining the closed non-deployed and maximum open positions of the aortic tissue retractor.

Figure 21:
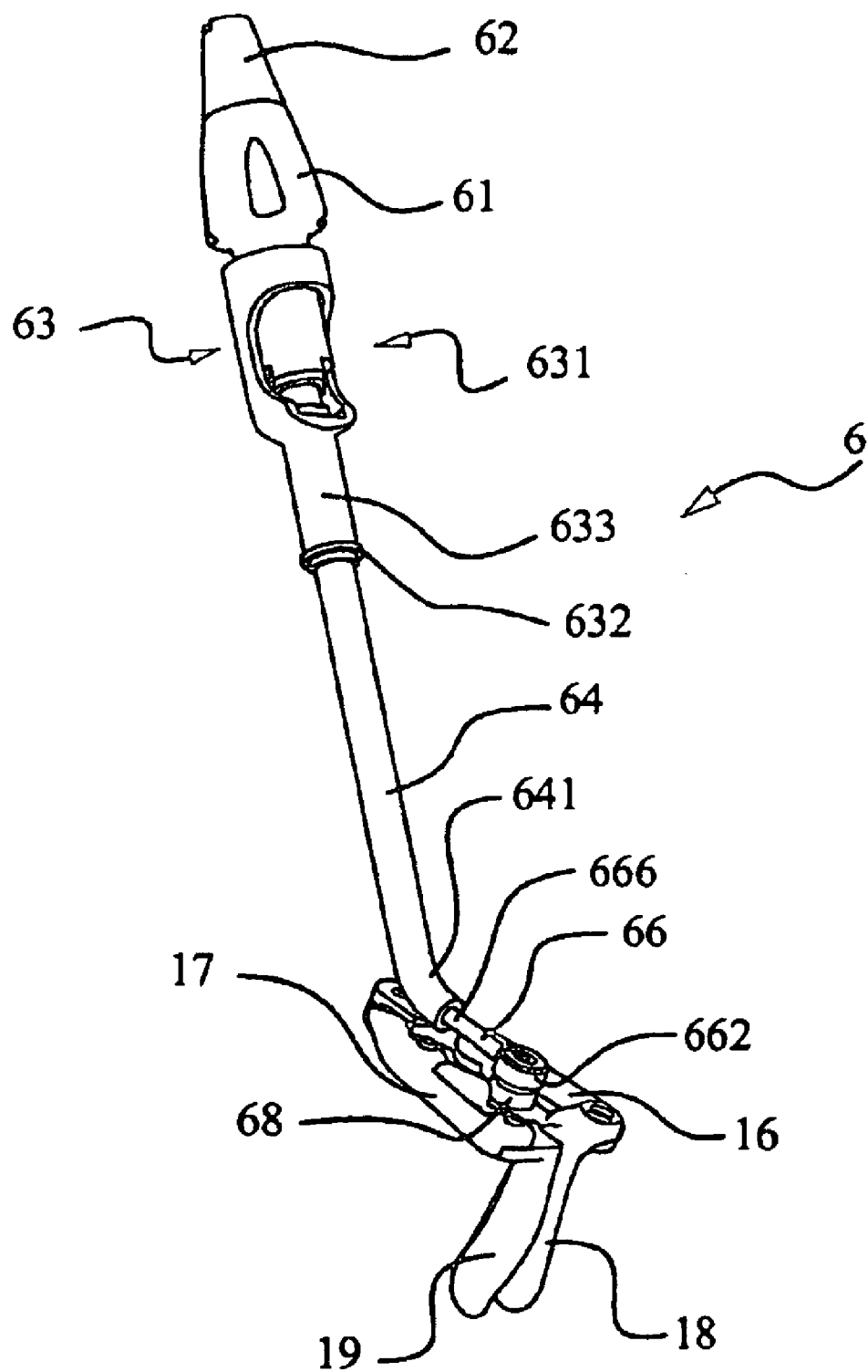
FIG. 21 is a perspective view of a variant valve surgery tool in the nature of an aortic tissue retractor according to the present invention provided with a proximal actuator and translating actuation member in the nature of a flexible cable.
Figure 22:
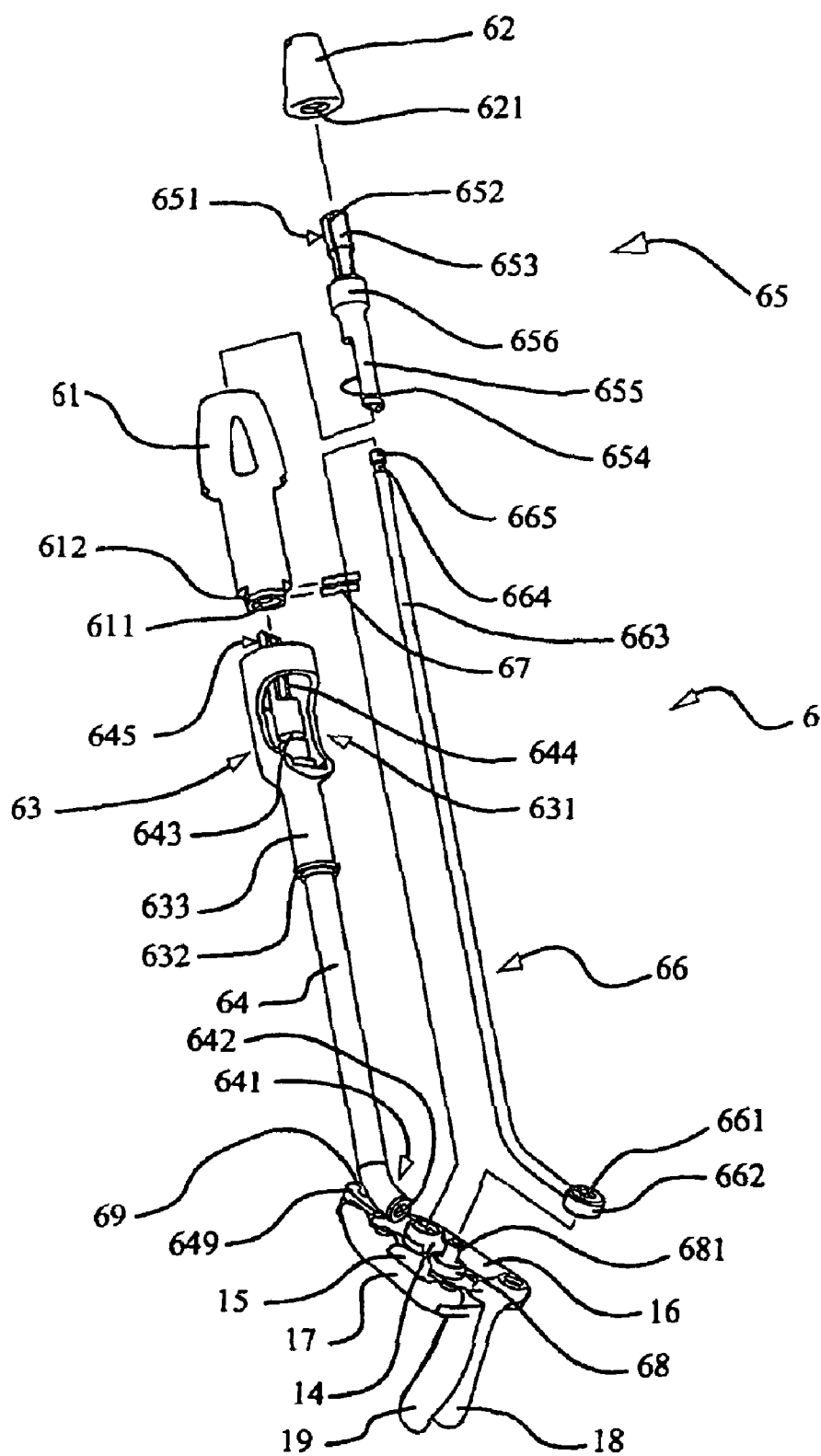
FIG. 22 is an exploded view of the valve surgery tool illustrated in FIG. 21.

Alternatively to aortic tissue retractor 1 described above, FIGS. 21 and 22 illustrate a variant aortic tissue retractor 6 according to the present invention which provides the advantage of a proximal actuator in the nature of actuator knob 61 in a bent tube 64 configuration. A translating actuation member in the nature of a flexible cable 66 is also provided to be housed mostly within said bent tube 64. Bend 641 may be produced in many different sizes depending on the surgical application and the associated surgical apparatus which may be used to secure or hold aortic tissue retractor 6. In all bent tube configurations, said actuator knob 61 is advantageously located proximal to the surgeon and remotely away from the surgical worksite.

Tissue engaging blades 18, 19, and 13 and a linkage arrangement comprised of actuating linkages 14, 15 and trailing linkages 16, 17 is similar to that described in the first embodiment. The clevis 123 and slot 136 arrangement in the first embodiment is replaced by a cylindrical adaptor 68. A cylindrical portion of adaptor 68 (not shown) extends through a series of aligned boles, one in each of inner blade 13, actuating linkages 14 and 15. This results in a mechanical joint assembly which pivotingly engages said blade 13 and said linkages 14 and 15.

Flexible cable 66 is comprised of a threaded collar 662 disposed at its distal free end, and a bulb protrusion 665 at its opposite proximal free end. Preferably, a low friction sheath 663 surrounds cable element 664 of flexible cable 66 with an aim to facilitate sliding of cable 66 within hollow passage 642 of tube 64 when inserted therewithin. The top portion of adaptor 68 is configured with threaded stud 681 which engages with inner thread 661 of collar 662 to provide a demountable cable assembly.

Bent tube 64 is configured with a fitting 649 at its distal free end. Said fitting serves to pivotingly engage trailing linkages 16, 17 through a common pivoting axis 69, in a similar manner as that described in the first embodiment. The opposite proximal free end of tube 64 is configured with a half tube or hemi-tubular portion 645. A circumferential groove 643 is disposed in tube 64, in general proximity to hemi-tubular portion 645. A substantially tubular handle 63 is fitted to the proximal end of tube 64. Handle 63 has a stepped configuration comprising a stepped down portion 633 whose inner diameter allows it to fit over the outer diameter of tube 64 at its proximal free end, and a larger diameter free end which allows the insertion of a portion of actuator knob 61 therein. Handle 63 is sufficiently inserted over tube 64 such that circumferential groove 643 is visible through handle window 631. Handle 63 is configured with a circumferential ridge 632 at the free end of its stepped down portion 633, allowing spherical clamp 32 of positioning and articulation mechanism 30 to advantageously engage aortic tissue retractor 6 on stepped down portion 633, in a location between window 631 and circumferential ridge 632. Alternatively, spherical clamp 32 may also engage aortic tissue retractor 6 along the straight tube portion of tube 64 below ridge 632 and above bend 641.

Handle 63, tube 64, and knob 61 form an integral assembly. Handle 63 may be preferably welded, brazed or mechanically mounted to the proximal free end of tube 64. Actuator knob inner bore 611 is inserted over hemi-tubular portion 645 and sufficiently over tube 64 such that openings 612 in actuator knob 61 are aligned with circumferential groove 643. Two pins 67 are inserted in transverse openings 612 thereby assuming an orientation that is perpendicular to the centerline axis of knob 61, but that is offset a certain distance from said centerline axis. When pins 67 are inserted in openings 612, at least a portion of said pins extends within inner bore 611 of knob 61 and rests within circumferential groove 643. Pins 67 are preferably welded or staked in place relative to knob 61. As such, knob 61 is rotatingly engaged with tube 64.

Actuator piston 65 is comprised of a hemi-tubular portion 655 at its distal free end, and a split collet 653 at the opposite proximal free end. Hemi-tubular portion 655 is configured with a longitudinal flat face 654 which is coincident with centerline axis of actuator piston 65. Split collet 653 is configured with a plurality of slits 652 that interrupt an external thread 651. Actuator piston 65 is also configured with a non-interrupted external thread 656 disposed between said split collet 653 and said hemi-tubular portion 655.

Inserting distal free end of actuator piston 65 into proximal free end of inner bore 611 will place into sliding engagement the cooperating hemi-tubular portions 655 and 645 along their longitudinal flat faces 654 and 644. Piston 65 is inserted sufficiently in order to bring into engagement external thread 656 with an internal thread (not shown) disposed along a portion of inner bore 611 of knob 61. At this point, a rotation of knob 61 results in a translation of actuator piston 65 relative to tube 64 with a sliding contact taking place along longitudinal flat faces 654 and 644. As such, actuator piston 65 is demountable engaged with the integral assembly comprised of actuator knob 61, bent tube 64 and handle 63.

Flexible cable 66 engages with threaded stud 681 of adaptor 68 through its threaded collar 662. Trailing linkages 16, 17 are displaced angularly to one side of tube 64 by pivoting about pivot axis 69 of fitting 649. Bulb end 665 of flexible cable 66 is now inserted into hollow passage 642 of tube 64. Flexible cable 66 is pushed through hollow passage 642 of bent tube 64, through hollow passageway created by cooperating hemi-tubular portions 655 and 645, and through inner passage (not shown) in actuator piston 65 in a manner to sufficiently expose said bulb end 665 outwardly beyond split collet 653. Cap nut 62 is configured with an internal thread 621 machined slightly smaller in pitch diameter than interrupted thread 651 on actuator piston 65. As such, when cap nut 62 is subsequently assembled on external thread 651, it causes the split collet 653 by virtue of slits 652 to compress radially upon cable element 664 which is housed within hollow passage in spilt collet 653. A demountable assembly comprising cap nut 62, actuator piston 65, and flexible cable 66 is thus formed. This demountable assembly is advantageous since it permits the cleaning and sterilization of hollow passage 642 and threaded interfaces between piston 65 and actuator knob 61.

Rotating actuator knob 61 causes actuator piston 65 to translate relative to tube 64, within inner bore 612 of said knob 61. Hemi-tubular portion 655 translates relative to cooperating hemi-tubular portion 645 while longitudinal flats 654 and 644 remain slidingly engaged. This translation of actuator piston 65 entrains a simultaneous translation of flexible cable 66 relative to tube 64 through hollow passage 642, since said cable is secured to said actuator piston by cap nut 62. Since cable 66 is engaged with adaptor 68 through collar 662, this translation of said cable relative to said tube entrains a simultaneous deployment of actuating linkages 14, 15 and consequently trailing linkages 16, 17.

Unlike the first embodiment which has a translating member in the nature of a rigid actuator piston 12, flexible cable 66 allows the linkage arrangement comprised of linkages 14, 15, 16, 17, along with pivotingly engaged blades 13, 18, 19, to pivot together as a deployed assembly about pivot axis 69. The amount of said pivoting will depend on the amount 666 which cable 66 extends outwardly from passage 642 beyond the distal free end of tube 64. As such, this flexibility provided by a flexible cable translating member allows a further degree of adaptability (relative to the first embodiment) of said deployed assembly in that the said deployed assembly is capable of assuming a more suitable orientation relative to tube 64, and relative to the cardiac tissue that is engaged with said blades.

Flexible cable 66 can be a metallic cable such as a braided stainless steel cable with a polymeric sheath casing, or a superelastic nitinol wire capable of repeatedly negotiating bend 641 in tube 64, or other like metalic cable member may also be used. Alternatively, cable 66 may also be constructed of non-metallic material or fibers.

Handle 63 allows the surgeon to manipulate aortic tissue retractor 6 whether said retractor is engaged or not with spherical clamp 32 of positioning and articulation mechanism 30. Window 631 advantageously allows the surgeon's thumb or finger to come into contact with a portion of knob 61 through said window, and restrain said knob from rotating during said surgeon manipulations.

Figure 10:
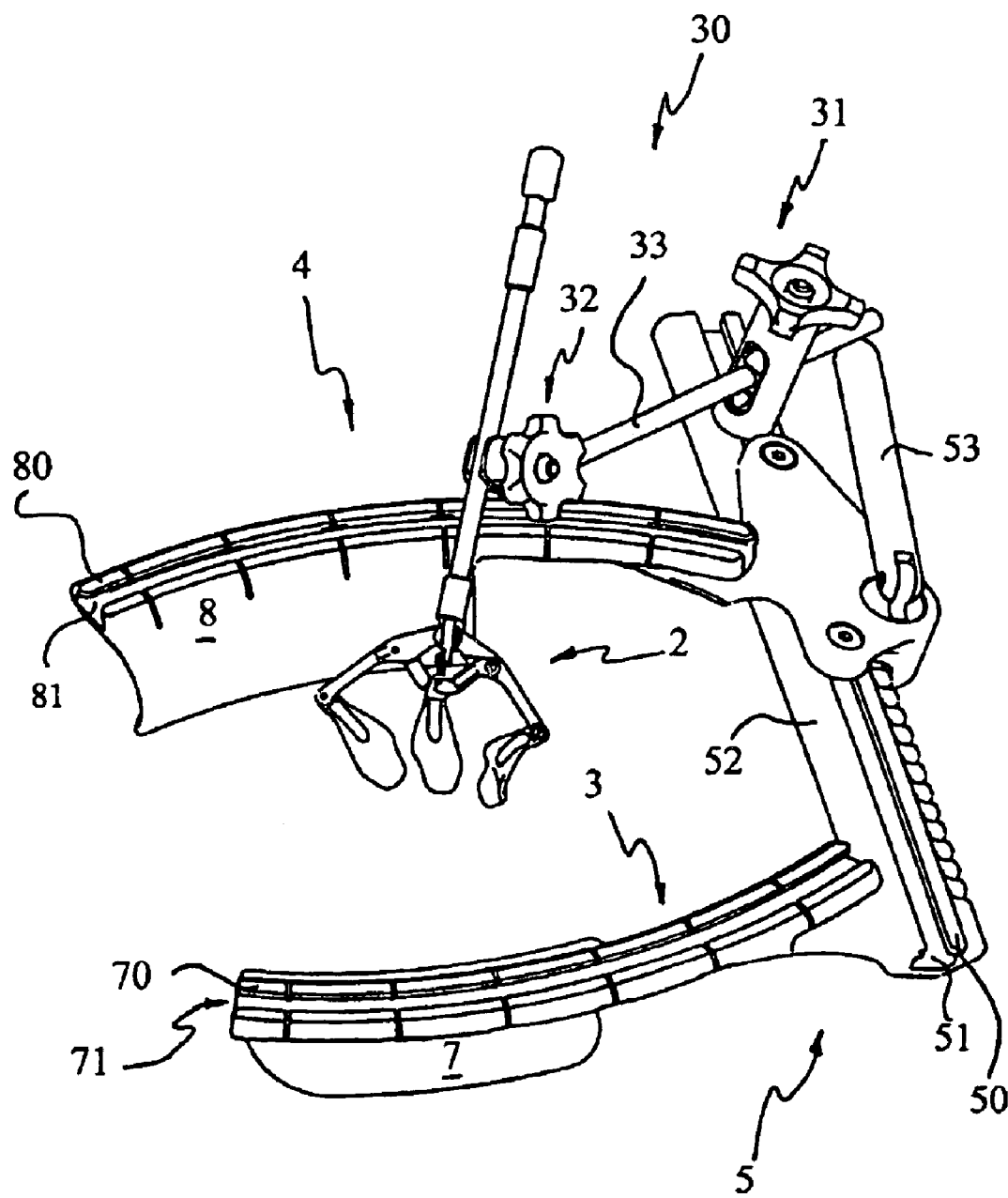
FIG. 10 is a perspective view of a surgical apparatus comprising a valve surgery tool according to a second embodiment of the present invention.
Figure 11:
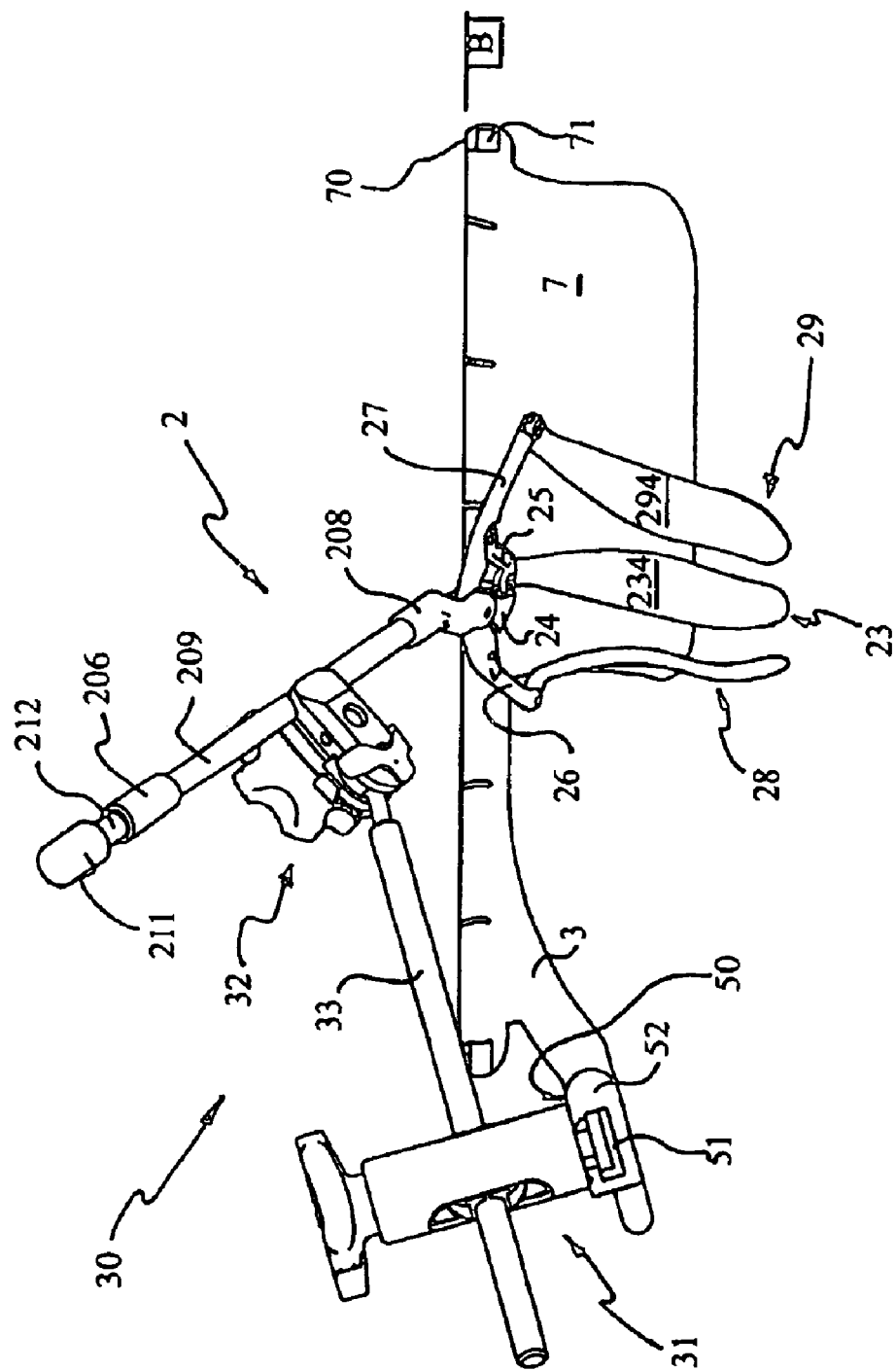
FIG. 11 is a side elevational view of a surgical apparatus comprising a valve surgery tool in the nature of an atrial tissue retractor according to a second embodiment of the present invention.
Figure 12:
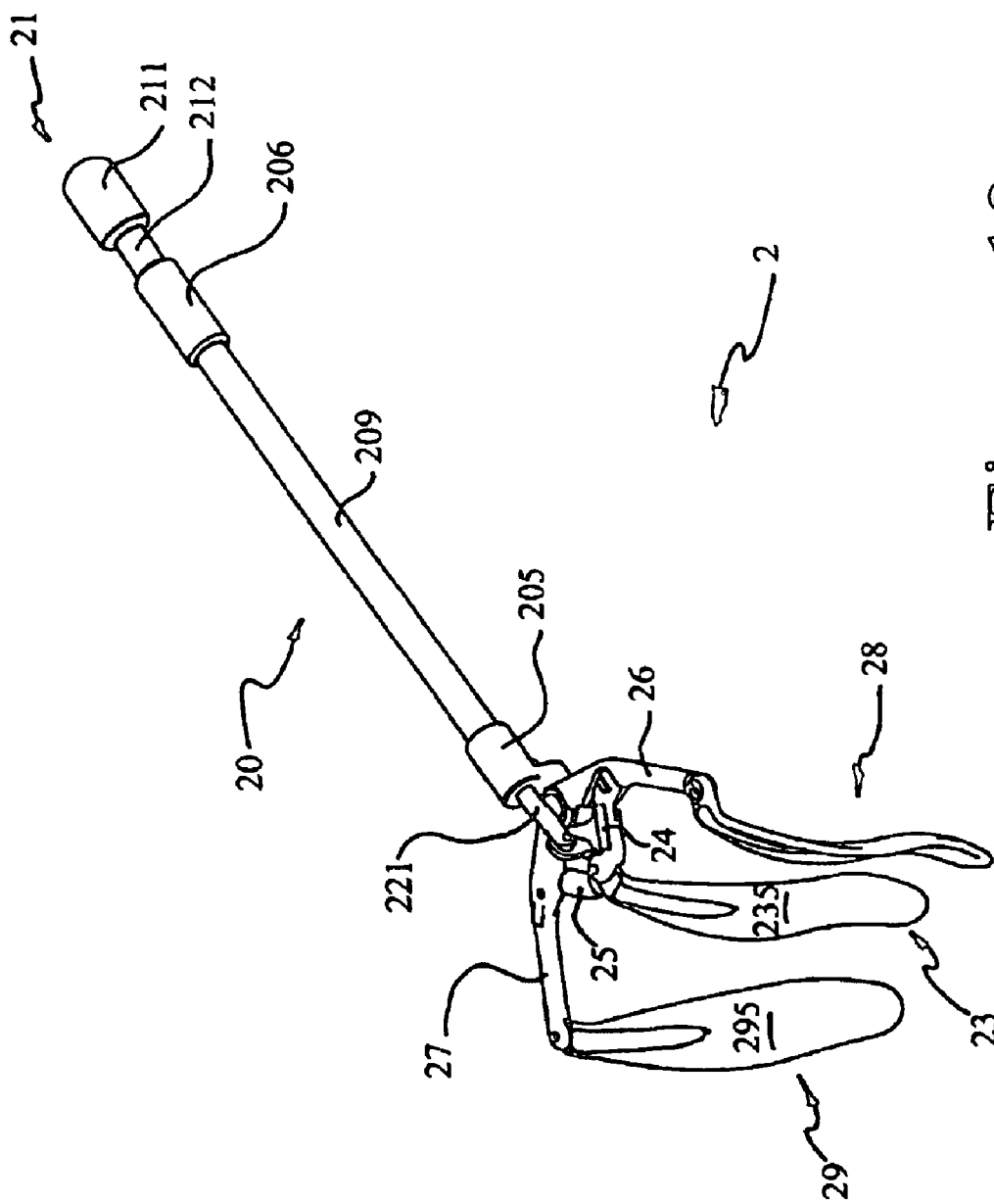
FIG. 12 is an isometric perspective view of a valve surgery tool in the nature of an atrial tissue retractor according to a second embodiment of the present invention.
Figure 13:
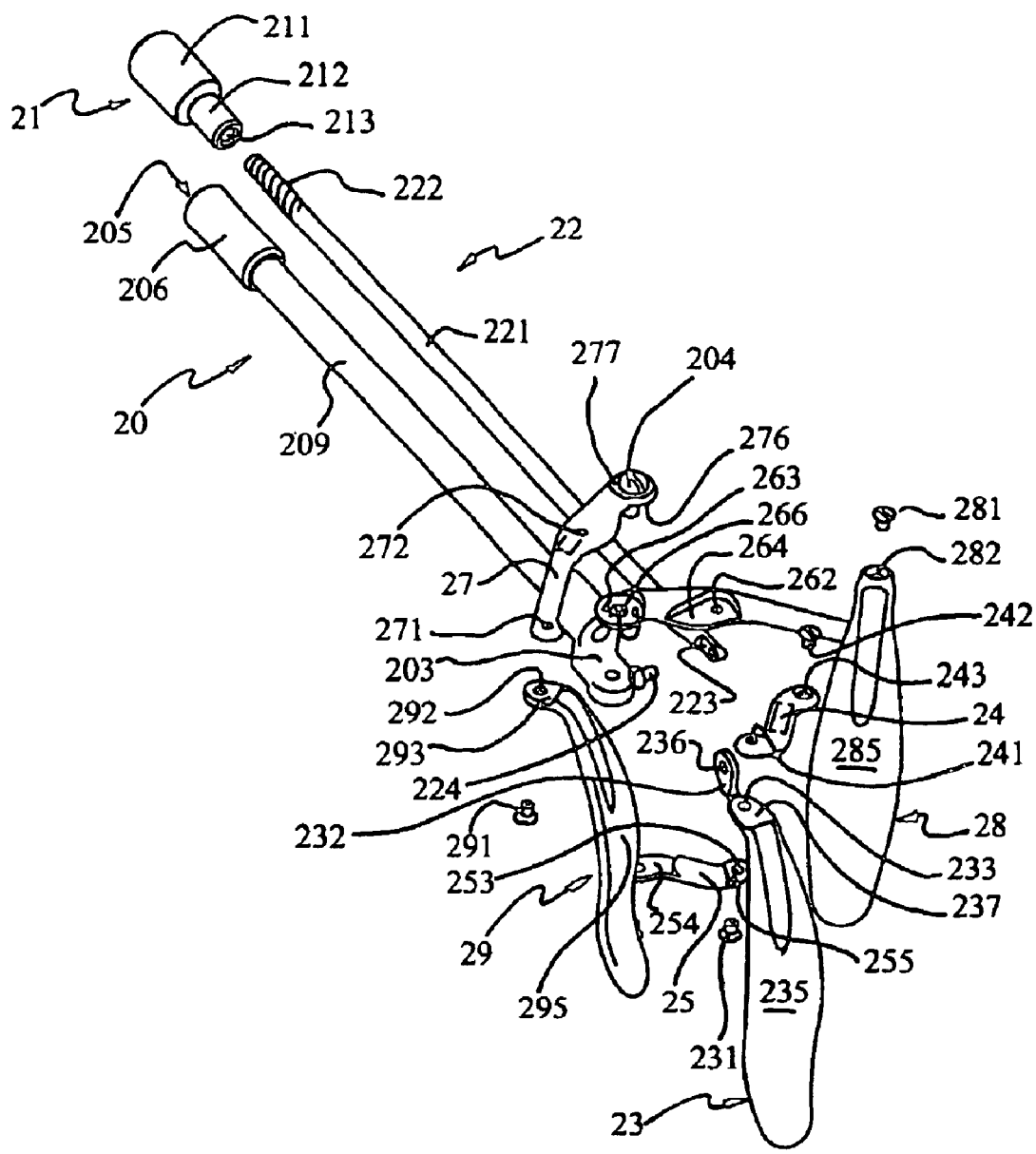
FIG. 13 is an exploded view of a valve surgery tool in the nature of an atrial tissue retractor according to a second embodiment of the present invention.
Figure 18:
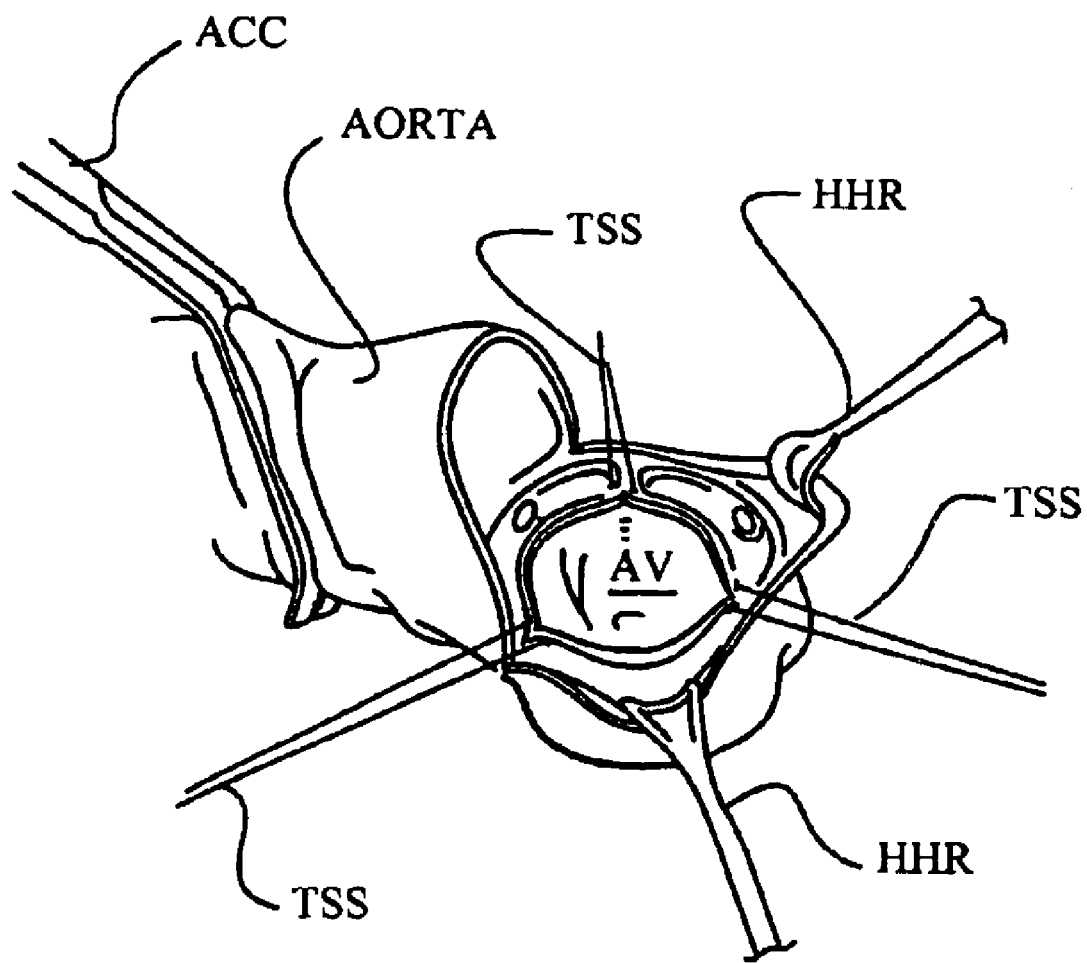
FIGS. 18–20 illustrate prior art surgery equipment to perform cardiac surgery.
Figure 19A:
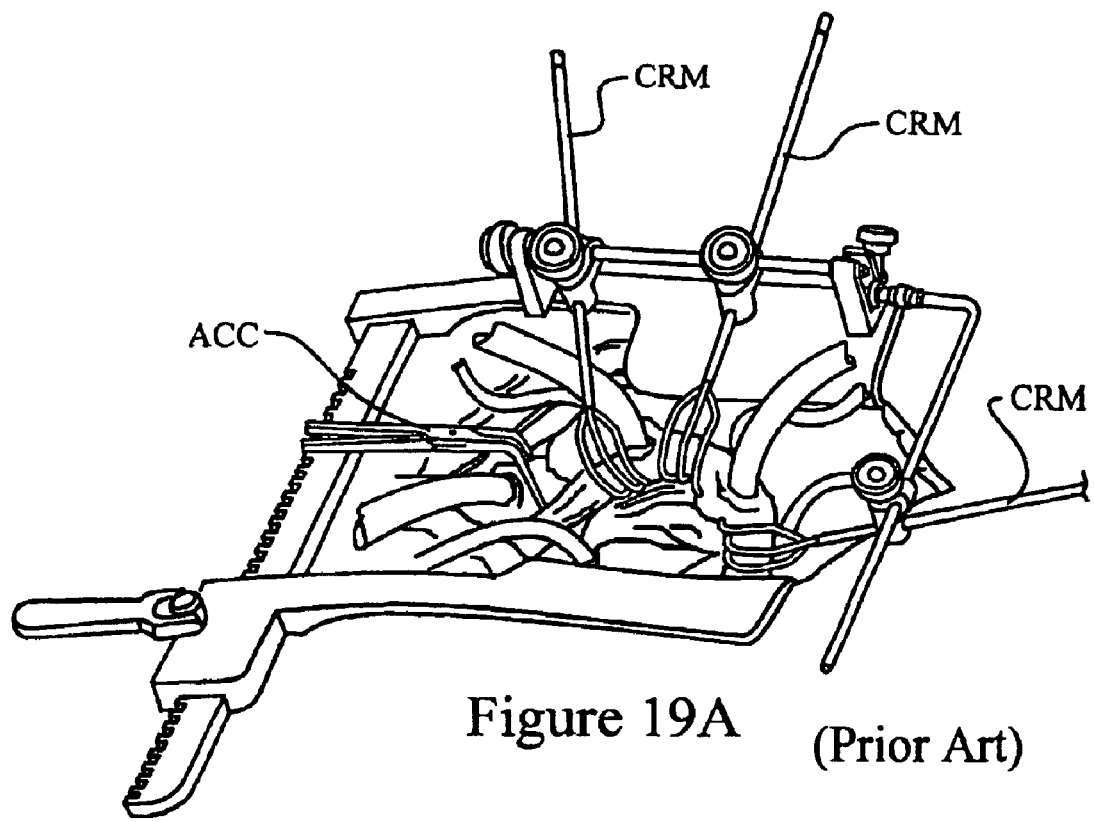
Figure 19B:
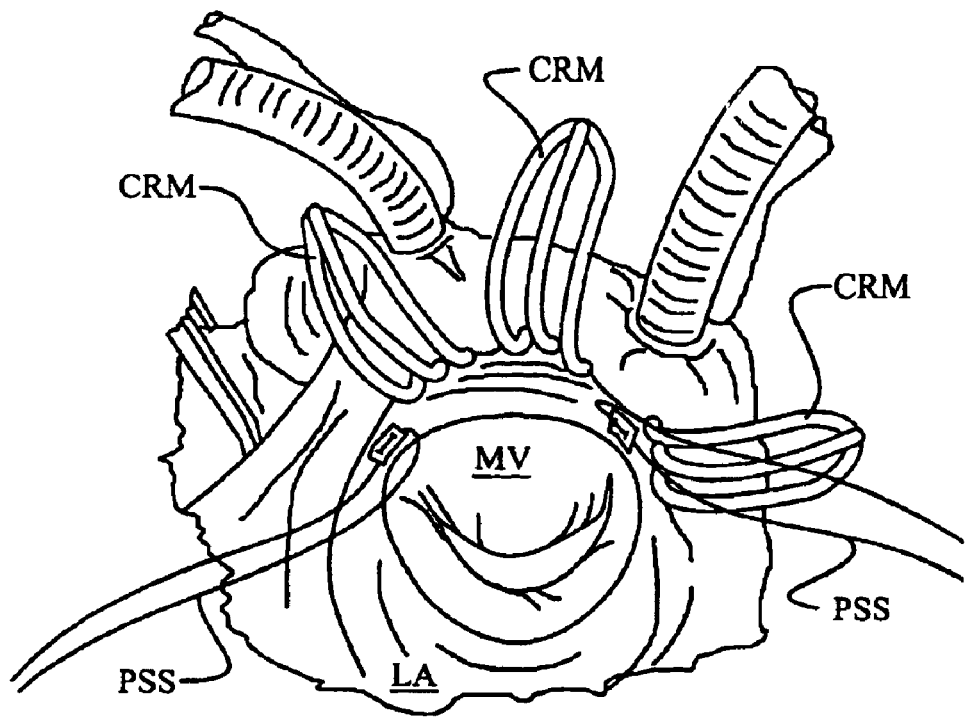
Figure 19C:
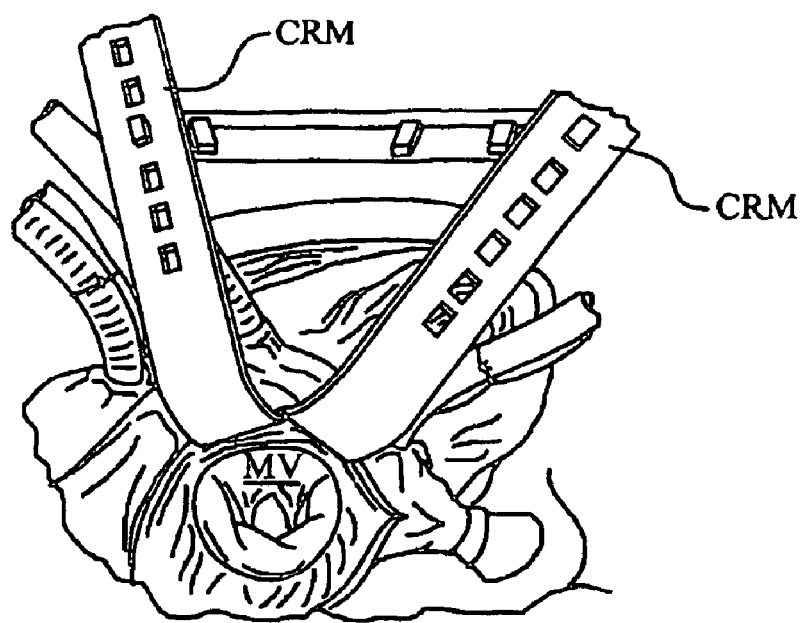
Figure 20:
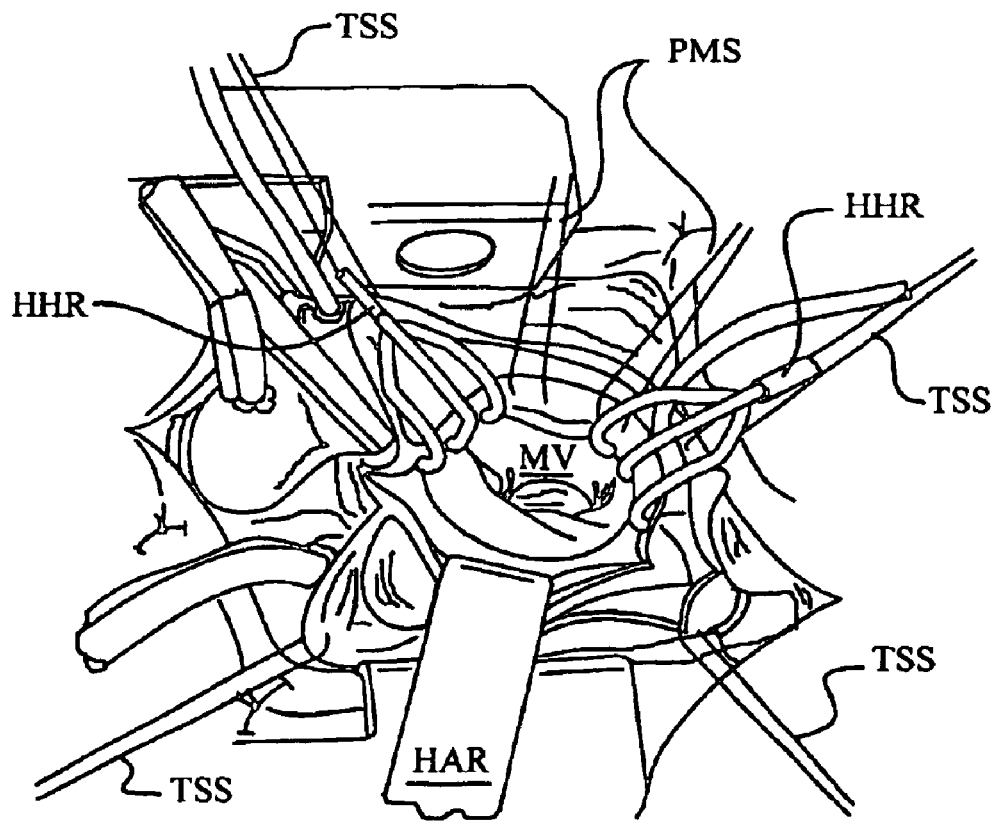

FIG. 10 illustrates a second embodiment of a valve surgery tool in the nature of an atrial tissue retractor 2 according to the present invention. Atrial tissue retractor 2 is intended to be utilized in mitral valve surgery, whether the mitral valve is approached through a left atrium approach or a combined right atrium, intra-atrial septal approach. Atrial tissue retractor 2 is comprised mainly of a housing 20, an actuator 21, a translating actuation member in the nature of actuating shaft 22, two actuating arms or linkages 24 and 25, two pivoting arms or trailing linkages 26 and 27, and three fingers or cardiac tissue engaging blades 23, 28, and 29.

The concepts and principles of the first embodiment as described above also apply to this second embodiment with several noted variations intended to optimize the atrial tissue retractor 2 for mitral valve surgery. The atrial tissue retractor 2 is configured with three cardiac tissue engaging blades 23, 28, and 29 that are larger, deeper-extending relative to plane D, and generally more robust than the blades of the aortic tissue retractor 1 of the first embodiment.

Once the atrial tissue retractor 2 is fully assembled, the top surfaces 249, 259, 269, 279 of linkages 24, 25, 26, and 27 respectively are contained and define a plane D (FIG. 15A).

In this second embodiment, actuating shaft 22 translates along an axis parallel to plane D (FIG. 15C). Actuating shaft 22 is comprised of a threaded portion 222 at its proximal free end, a rod portion 221, and a flange 223 at the opposing distal free end. Actuator 21 is configured with an external thread 212 and a concentric internal thread 213. As such, when assembled, actuator 21 operatively engages both the internal thread 205 in housing fitting 206, and the external thread 222 of shaft 22 through a rotation (surgeon input) of actuation knob 211. As with the first embodiment, the type and definition of said threads provides an arrangement that allows the translation of shaft 22 (and, in use, also of blade 23) to be amplified or reduced relative to the translation of actuator 21. The distal end of shaft 22 is connected to plate 232 of center blade 23 by assembling screw 224 through hole 236 of said plate.

In this embodiment, actuating linkages 24, 25 are preferably identical. Said actuating linkages are pivotingly engaged with translating center blade 23 in a similar fashion as the first embodiment. Screw 231 is inserted in countersink hole 253 through hole 233 and threaded into tapped hole 241. The shank of screw 231 acts as a pin or axle. Flat surfaces 255 of said linkages 24, 25 are rotatingly engaged with two parallel faces 237 on blade 23 which act as bearing faces serving to guide the rotation of said actuating linkages. The opposing ends of said linkages 24, 25 are pivotingly engaged with trailing linkages 26, 27 in a similar fashion as the first embodiment. Trailing linkages 26, 27 are preferably identical. Screw 242 is inserted in countersink hole 243 of linkage 24 and acts as a pin or axle when threaded into tapped hole 262 (or 272) of trailing linkage 26 (or 27). Bearing faces 254 and 264 are thus rotatingly engaged. Blades 29 and 28 are pivotingly engaged to distal free ends of trailing linkages 27 and 26, respectively. Screws 281 and 291 act as pins or axles for blades 29, 28, respectively when inserted through holes 292, 282 and threaded into tapped hole 271. The proximal free ends of trailing linkages 26, 27 are pivotingly engaged with housing 20 through a common pivoting axis coincident with the centerline of screw 204 which acts as a pin or axle when inserted through holes 263 in each of said trailing linkages and threaded into a tapped hole in proximal fitting 203 of said housing. As such, faces 266 and 276 are rotatingly engaged and act as bearing faces serving to guide the pivoting motions of said trailing linkages. Flat face 277, which is parallel to face 276 on said linkage 27, mates with pan head screw 204. An identical flat face (not shown) on linkage 26 mates with a flat face on fitting 203 to guide the deployment of the linkage arrangement comprising linkages 24, 25, 26, 27 along a plane parallel to plane D.

In this second embodiment, actuator 21 is disposed proximally to the surgeon and configured on the proximal end of housing 20. The actuating linkages 24 and 25, and trailing linkages 26 and 27 are disposed on the distal end of housing 20. Actuating shaft 22 serves to transmit the surgeon input in the form of a rotation of actuating knob 211 to a distal translation of center blade 23 in a direction parallel to plane D. The translation of center blade 23 entrains the simultaneous and opposing rotations of actuating linkages 24 and 25 and consequently the simultaneous and opposing rotations of trailing linkages 26 and 27. The opposing rotations of trailing linkages 26 and 27 cause the blades 28 and 29 to move apart in a direction also parallel to plane D. All said rotations occur along plane D.

In this second embodiment, the longitudinal axis of second articulation rod in the nature of a tubular member 209 is coincident with the common longitudinal axis through actuator 21 and actuating shaft 22.

The closed, non-deployed configuration and the open, maximum deployed configuration of the atrial tissue retractor 2 are defined with reference to FIGS. 14A and 14B, respectively. To facilitate insertion of atrial tissue retractor 2 the tissue-engaging blades 23, 28, 29 are capable of assuming a generally compact arrangement with a relatively small substantially circular radius of retraction R=R3 and a relatively small circumference of retraction C=C3 in the closed, non-deployed configuration. The angle between trailing linkages 26, 27 in this generally compact arrangement is $\phi 3$, and the pivot orientation of blades 28, 29 when substantially engaged with cardiac tissue is $\beta 3$. Through the rotation of the actuation knob 211, and the resultant translation of actuating shaft 22 and center blade 23, trailing linkages 26, 27 and actuating linkages 24, 25 rotate apart and provide a substantially continuous range of variable intermediate positions or settings defined by R, C, $\beta$, and $\phi$ up until the maximum deployed position of atrial tissue retractor 2 is reached and defined by R4, C4, β4, and φ4. The open, maximum deployed position is designed to attempt to cater for the maximum size atrial incision generally encountered during mitral valve surgery. In between these two limit configurations, that is, the non-deployed and maximum deployed positions, the atrial tissue retractor 2 may be selectively adapted to attempt to cater to the entire spectrum of different size atrial and intra-atrial septum incisions generally encountered during mitral valve surgery as a function of patient variability. This tends to allow the atrial tissue retractor 2 to be adapted to whatever specific surgical incision or patient anatomy the surgeon is presented with, thereby also tending to improve surgical access to a diseased valve.

When not engaged with cardiac tissue, blades 28 and 29 of a fully assembled atrial tissue retractor 2 are free to pivot about their respective pivot axis within a range of β between 90 and −90 degrees. During mitral valve surgery, the incision in atrial or intra-atrial septum cardiac tissue is generally linear or slightly arcuate. As the two halves of the incision are retracted, the curvature increases and the resulting opening between the two halves of the incision increases resulting in the exposure of the diseased valve. The pivotingly engaged blade 28, 29 design allows tissue retraction loads on atrial or intra-atrial septum cardiac tissue to be applied in substantially perpendicular orientation to the engaged portion of incised cardiac tissue. Moreover, as the incision is progressively retracted by the deployment of the atrial tissue retractor 2, the curvature along the incision varies continuously. The pivotingly engaged blades 28 and 29 reorient themselves such that the retraction loads are still applied in a generally perpendicular orientation relative to the portion of cardiac tissue engaged with said blades throughout the entire range of deployed configurations the atrial tissue retractor 2 is capable of assuming. This tends to minimize likelihood of tissue trauma and tearing at the incision extremities where the two halves of the incised tissue meet.

In a specific example of an atrial tissue retractor the definition of the variables at the non-deployed closed configuration and corresponding maximum open configuration is as follows: R3=0.595 in., R4=1.435 in., C3=0.830 in., C4=1.755 in., φ3=35 degrees, φ4=82 degrees, β3=55 degrees, β4=75 degrees, d6=0.915 in., d7=0.645 in., d8=0.990 in., and d9=1.585 in. These values are approximate.

The contacting surfaces 234, 284, 295 and non-contacting surfaces 235, 285, 295 of blades 23, 28, and 29 respectively are identical in this second embodiment. FIGS. 16A–16C illustrate the definition of the contact 234 and non-contact 235 surfaces of center blade 23, and by similarity also the definition of blades 28 and 29. The extending-most point of blades 23, 28, 29 relative to their respective pivot axis is identified as point Z, which is preferably bent away from the contacting surfaces 234, 284, and 294 to avoid concentrated loads exerted on cardiac tissue during the insertion of atrial tissue retractor 2 into the surgical incision and during subsequent retraction. This tends to avoid the likelihood of piercing cardiac tissue with the extending most portions of blades 23, 28, and 29.

Blades 23, 28, and 29 are sufficiently long (L7) in order to be able to engage simultaneously cardiac tissue from the right atrium and intra-atrial septum in a mitral valve procedure that employs the right atrium/intra-atrial septum approach. Blade 23 extends below plane E in a substantially normal orientation to said plane E. The extending-most point Z is offset a distance L7 below plane E and distance d6 away from the centerline defining hole 233. Plane E is parallel to plane D and lies slightly below plane D. Section plane 16B—16B, located a distance L9 above point Z, provides a cross-section parallel to plane E as illustrated in FIG. 16B. The radius of curvature of non-contact surface 235 in this cross-sectional plane is identified as r15. A section plane 16C—16C through the mid-span width of blade 23 provides a cross-sectional view through said blade 23, where said section 16C—16C is perpendicular to plane E. The non-contact surface 235 of blade 23 is preferably generated by defining a cross-sectional profile in section plane 16C—16C, and revolving said cross-sectional profile about an axis of revolution AR3 as illustrated in FIG. 16C. The contact surface 234 is defined by offsetting the resulting non-contact surface 235 by a distance equal to the blade 23 thickness. This offset need not be a parallel offset if the blade 23 is of variable thickness.

The cross-sectional profile in section plane 16C—16C of the non-contact surface 235 of blade 23 is substantially s-shaped and generally defined by three radii r16, r17, and r18. The inflection in this said profile (from convex close to plane E to concave close to point Z) results in an inflected shape on the contact surface 234 (concave close to plane E to convex close to point Z) which helps to maintain or support cardiac tissue engaged during tissue retraction. Moreover, the revolution of this inflected contact profile about axis AR3 tends to avoid sharp edges along the lateral edges of the blade 23. The width of blade 23 is the resultant distance between lateral edges of said blade, said lateral edges defined by r13 and r14 in FIG. 16A. The maximum width of said balde is W3.

In a specific example of an atrial tissue retractor advantageously configured to maintain or support atrial tissue, the definition of the tissue engaging blades 23, 28 and 29 is as follows: L7=2.200 in., L8=0.105 in., L9=0.750 in., W3=0.555 in., r13±0.375 in., r14=3.861 in., r15=0.560 in., r16=0.150 in., r17=2.50 in., r18=1.000 in., d6=0.915 in. These values are approximate.

FIGS. 17A–17C illustrate yet another example of the atrial tissue-engaging blades with a substantially C-shaped cross-sectional profile. The definition of the contact 434 and non-contact 435 surfaces of center blade 43, and by similarity also the definition of the two other outer blades 48 and 49 (not shown). The extending-most point of blades 43, 48, 49 relative to their respective pivot axis is identified as point W, which is in this example preferably bent away from the non-contacting surface 434 tending to hook or cup or maintain into engagement the cardiac tissue while retraction loads are exerted on said cardiac tissue when said tissue engaging blades are deployed along a surgical incision.

Blades 43, 48, and 49 are sufficiently long (L10) in order to be able to engage simultaneously cardiac tissue from the right atrium and intra-atrial septum in a mitral valve procedure that employs the right atrium/intra-atrial septum approach or may also be tailored for a left atrium approach. Blade 43 extends below plane E in a substantially normal orientation to said plane E. The extending-most point W is offset a distance L10 below plane E and distance d7 away from the centerline defining hole 433. Plane E is parallel to plane D and lies below plane D. Section plane 17B—17B, located a distance L12 above point W, provides a cross-section parallel to plane E as illustrated in FIG. 17B. The radius of curvature of non-contact surface 435 in this cross-sectional plane is identified as r21. A section plane 17C—17C through the mid-span width of blade 43 provides a cross-sectional view through said blade 43, where said section 17C—17C is perpendicular to plane E. The non-contact surface 435 of blade 43 is preferably generated by defining a cross-sectional profile in section plane 17C—17C, and revolving said cross-sectional profile about an axis of revolution AR4 as illustrated in FIG. 17C. The contact surface 434 is defined by offsetting the resulting non-contact surface 435 by a distance equal to the blade 43 thickness. This offset need not be a parallel offset if the blade 43 is of variable thickness.

The cross sectional profile in section plane 17C—17C of the non-contact surface 435 of blade 43 is substantially C-shaped and generally defined by three radii r22, r23, and r24. The C-shaped cross-sectional profile helps to support cardiac tissue engaged during tissue retraction. Moreover, the revolution of this contact profile about axis AR4 tends to avoid sharp edges along the lateral edges of the blade 43. The width of blade 43 is the resultant distance between lateral edges of said blade as defined by r19 and r20 in FIGS. 17A and 17B.

In this other example illustrated in FIGS. 17A–17C, of an atrial tissue retractor advantageously configured to hook atrial tissue, the definition of the tissue engaging blades 43, 48 and 49 is as follows: L10=1.400 in., L11=0.095 in., L12=0.630 in., W4=0.475 in., r19=0.200 in., r20=2.500 in., r21=0.350 in., r22=0.060 in., r23=1.725 in., r24=0.130 in., d7=0.120 in. These values are approximate.

In broad terms, a surgical procedure for the set-up of a surgical apparatus with which the atrial tissue retractor 2 may be used during a mitral valve surgery approached through a left atrial incision, and relating to the present invention, preferably consists of:

(a) Performing a partial or midline sternotomy incision;
(b) Cauterizing any bleeding vessels subsequent to the sternotomy incision;
(c) Retracting the patient's ribcage through the deployment of sternum retractor 5;
(d) Placing the patient on cardiopulmonary bypass through the cross-clamping of the aorta and the installation of a series of cannulae to obtain aortic cannulation, bicaval cannulation and cannulation to administer cardioplegia;
(e) Incising the pericardium slightly to the right of the midline to expose the underlying heart surface;
(f) Applying pericardium retraction sutures to the right side of the incised pericardium to help provide elevation of the right side of the heart;
(g) At times, placing a tourniquet on the inferior vena cava and applying traction towards in the general direction of the patient's feet to help elevate the right side of the heart;
(h) Incising the left atrium parallel to the intra-atrial groove, and if necessary extending the incision below the superior vena cava and a considerable distance below the inferior vena cava;
(i) Installing the cylindrical post 31 of positioning and articulation mechanism 30 on sternum retractor 5 at an approximate location along the perimeter rails (50, 70, or 80) suitable for the patient's specific anatomy and surgeon work preference, typically along rack bar 52 of the sternum retractor 5;
(j) While holding the atrial tissue retractor 2 by the tubular member 209, inserting the cardiac tissue engaging blades 23, 28, 29 in their closed configuration into the left atrial incision and engaging the contact surfaces 234, 284, 294 of said blades along the left side of said atrial incision;
(k) While gently applying retraction in the vector direction to best obtain exposure to the mitral valve, rotating actuator knob 211 sufficiently to deploy the atrial tissue retractor 2 to a suitable open position whereby the tissue engaging blades 23, 28, 29 assume a generally dispersed setting along the length of the atrial incision (creating the surgical worksite);
(l) Engaging the proximal end of tubular member 209 into the open ended spherical clamp 32 while gently maintaining the magnitude of the retraction load and the direction vector of the retraction load on the atrial tissue retractor 2;
(m) Slow and alternate tightening of each of the tensioning knobs of the cylindrical post 31 and spherical clamp 32 of the positioning and articulation mechanism 30 until the surgical setup is secured and fixed;
(n) Deploying the atrial tissue retractor 2 further towards its open maximum deployed configuration through the rotation of actuating knob 211 (re-adjustment of radius of retraction R, circumference of retraction C, and surgical worksite);
(o) If required, readjustment of the magnitude of retraction load or the vector direction of retraction load through the loosening of tensioning knobs of the cylindrical post 31, spherical clamp 32, or both followed by a readjustment of the arrangement of the positioning and articulation mechanism 30;
(p) Performing the mitral valve surgical intervention;
(q) Once the intervention has been completed, rotating the actuator knob 211 to relieve the retraction load slightly on the engaged cardiac tissue by returning blades 23, 28, 29 of the atrial tissue retractor 2 towards their closed position;
(r) Loosening tensioning knob of the spherical clamp 32 and disengaging the atrial tissue retractor 2 from said spherical clamp of the positioning and articulation mechanism 30;
(s) gently retrieving the atrial tissue retractor 2 from the incised atrium;
(t) closing the atrial incision;
(u) taking the patient off cardiopulmonary assistance;
(v) closing retractor arms 3 and 4 and retrieving sternum retractor 5;
(w) closing the partial or midline sternotomy incision.

If the mitral valve is to be accessed through a transeptal approach via the right atrium, steps (f) and (g) in the above described procedure are avoided and step (h) is replaced with: incising the right atrium followed by an incision in the intra-atrial septum to obtain access to the left atrium and the mitral valve.

The concepts and principles described above as they relate to valve surgery performed via a trans-thoracic approach may apply equally to surgeries which may be performed through trans-abdominal approaches.

In the embodiments of the present invention described herein, it is intended to produce the bulk of the surgical apparatus from reusable components, whose assembly may be at least partially dismantled, if necessary, for ease of sterilization. All components are manufactured in either surgical grade stainless steel, titanium, aluminum or any other reusable sterilizable material suitable for surgical use. Components that may be produced from polymeric materials are either reusable through specific sterilization procedures tailored to these component materials, or must be replaced after every use or after a predetermined number of uses if the polymeric material properties are not suitable for sterilization or degrade after repeated sterilization cycles. However, any number of the said reusable components may also be produced from disposable surgical grade plastics, if the case for disposable components is warranted and if the engineering and functional intent is maintained when said component is produced from plastic.

In the above described embodiments, a cardiac tissue is mechanically engaged or mechanically retracted by one or more fingers or tissue-engaging blades of a valve surgery tool. The geometry of the said tissue engaging blades is configured to allow the valve surgery tool to maintain or modify an opening in cardiac tissue, or to retract or displace cardiac tissue with the aim of providing access and visibility to a surgical intervention site or surgical worksite. Generally, the said opening in cardiac tissue is at least partially flanked by the said tissue-engaging blades.

Figure 23:
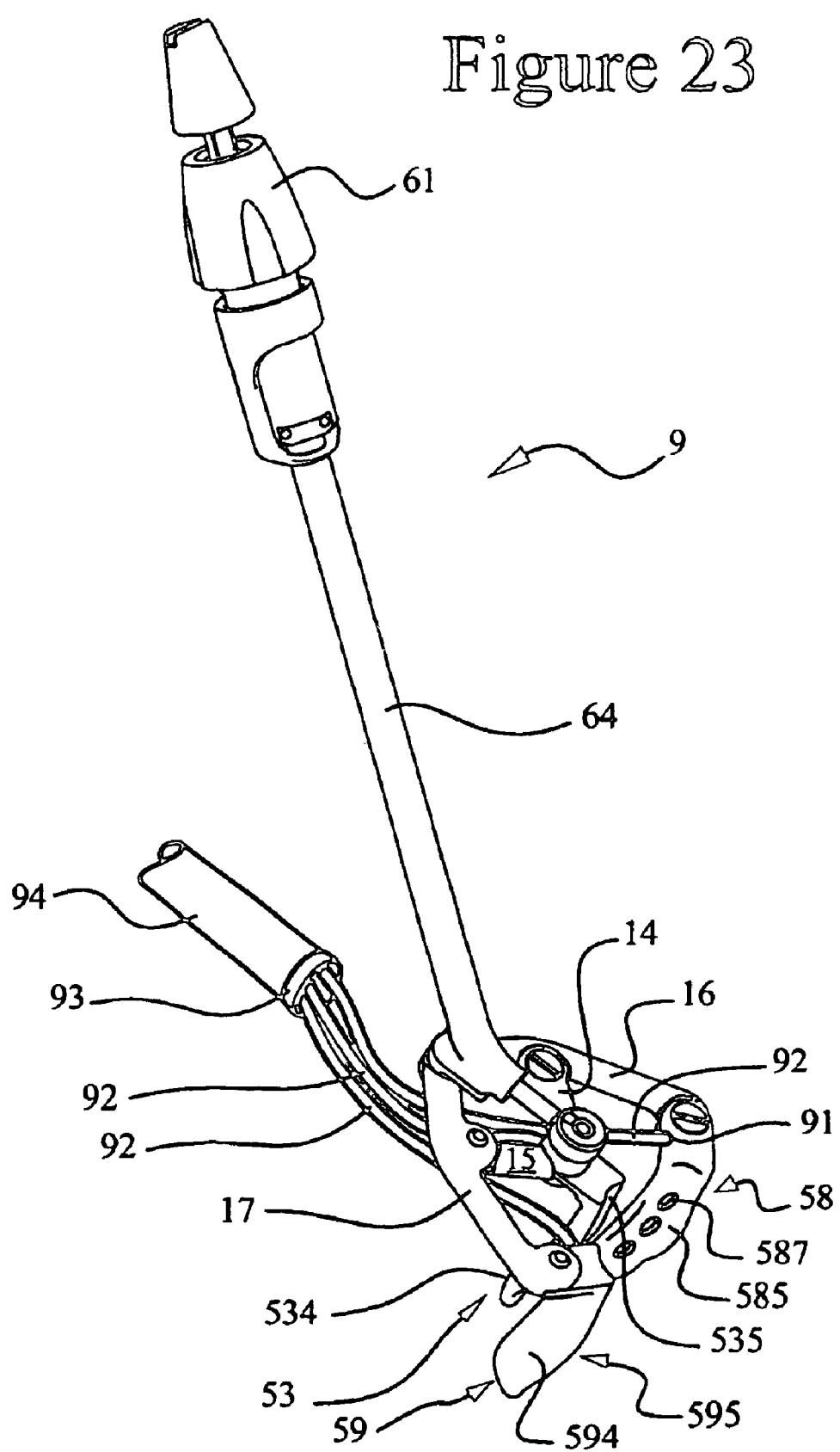
FIG. 23 is a perspective view of a valve surgery tool according to a third embodiment of the present invention provided with suction apertures on cardiac tissue engaging blades.

In a third embodiment according to the present invention, a cardiac tissue is engaged or retracted by virtue of a negative pressure suction force. FIG. 23 illustrates a valve surgery tool in the nature of aortic tissue retractor 9 having at least one suction aperture 587 provided on the contact surface 585, 535, or 595 of tissue-engaging blade 58, 53, or 59 and adapted to cooperate with aortic tissue. Blades 58, 53, 59 are similar in geometry to blades 18, 13, 19 but their respective contact and non-contact surfaces are reversed relative to each other. For example, contact surface 194 of blade 19 is similar in geometry to non-contact surface 594 of blade 59.

During deployment of aortic tissue retractor 9, the contact surfaces 585, 535, and 595 engage the outer surface of an aorta in the vicinity of an aortotomy incision by virtue of a negative pressure suction force transmitted through said suction apertures. While engaged with said aortic tissue, blades 58, 53, and 59 cooperate to retract the incised aorta tissue and maintain a circular or tubular anatomic configuration of the aorta thereby providing access to the diseased aortic valve. This suction arrangement enables the placement of said tissue-engaging blades or fingers on the outside of the aorta, therefore providing more free space within the lumen of the aorta, or in the surgical worksite. The suction effect, applied on a less sensitive portion of the aorta also tends to reduce the risk of trauma. As such, aortic tissue retractor 9 may prove advantageous in delicate surgical interventions to be carried out on a diseased aorta, such interventions which are best performed without contacting the inner lumen of said diseased aorta.

The relative positions and orientations of blades 58, 53, and 59 may be modified and set to best suit a distinct anatomy of aorta by actuating cooperating linkages 14, 15, 16, and 17 through actuator knob 61, in a manner similar to that described in previous embodiments.

Blade 58 is illustrated with three substantially circular suction apertures 587. Other variants may also exist. For instance, the number of suction apertures, their size, their geometry, and their relative position along contact surface 585 may vary. Blade 58 (and similarly blade 53 and 59) is of a hollow configuration or configured with an internal passageway or channel (not shown) that communicates aperture 587 with port 91. Port 91 is preferably located on blade 58 in a location remotely away from suction aperture 587, and is configured to engage a flexible hollow suction line 92. The interface between suction line 92 and port 91 forms a substantial seal and is preferable demountable in order to facilitate cleaning and sterilization of hollow passageway in blade 58, and allow for the replacement of suction line 92, if required. A similar arrangement is provided on blades 53 and 59, each engaged with a discrete suction line 92. Each of the three suction lines 92 connect at a common manifold 93, which is in turn connected to a common main suction line 94. The length of each of the discrete suction lines 92 is such that the free movement of blades 58, 53, and 59 is not hindered by the said suction lines, throughout the entire range of settings from the closed configuration to the deployed, open configuration of the aortic tissue retractor 9. Main suction line 94 is connected to a negative pressure source or vacuum apparatus as commonly available in most operating rooms. Once the main suction line 94 is connected to the vacuum apparatus, a vacuum circulation is provided within said suction lines and within the hollow part of said tissue-engaging blades. A flow shut-off or flow control valve may be disposed on suction line 94 or on individual suction lines 92 to allow a surgeon the ability to shut off the vacuum circulation or to vary its intensity.

Alternatively, blades 58, 53, and 59 may not be configured in a similar manner relative to the location of their suction apertures. For example, in one variant, inner blade 53 may engage aortic tissue with suction apertures disposed on surface 534, while outer blades 58, 59 may engage aortic tissue with suction apertures disposed on surfaces 585, 595.

Alternatively, one or more suction apertures may also be disposed on contact surfaces 194, 134, or 184 of aortic tissue retractor 1 (first embodiment). As such, the said suction apertures may serve to enhance the adherence of the engaged cardiac tissue to the blades of the aortic tissue retractor. Said negative pressure suction apertures may also replace or cooperate with the mechanical friction effect of non-traumatic texture 197, if such texture is disposed on said contact surfaces. Consequently, cardiac tissue may be mechanically retracted or displaced while said tissue is encouraged to remain in engagement with said tissue-engaging blades by virtue of a negative pressure suction force available through said suction apertures. In a similar manner, one or more suction apertures may also be disposed on contact surfaces 294, 234, or 284 of atrial tissue retractor 2 (second embodiment) to engage atrial tissue.

The above description of the embodiments of the present invention should not be interpreted in any limiting manner since variations and refinements are possible without departing from the spirit of the invention.

What is claimed is:

1. A surgical tool for retracting body tissue during surgery, said surgical tool comprising:
   a first pivoting arm, a second pivoting arm, and a translating actuation member;
   said first arm and said second arm being respectively provided with a first finger and a second finger attached thereto generally adjacent a respective free end portion thereof;
   a third finger, said third finger operatively coupled to said surgical tool;
   said first arm, said second arm, and said actuation member being operatively connected together for substantially simultaneous movement therebetween between a closed configuration wherein said first finger, said second finger, and said third finger are in a generally proximate relationship relative to each other, and an open configuration wherein said first finger, said second finger, and said third finger are in a generally spaced relationship relative to each other;
   a single actuator mechanically coupled to either one of said first arm, said second arm, or said actuation member for allowing movement of said first arm, said second arm and said actuation member between said closed and open configurations, said movement occurring substantially in a tissue rotation plane;
   said actuator being actuated by a rotational force applied about an axis of rotation, said axis of rotation having a fixed spatial relationship relative to said plane of tissue retraction;

whereby upon said rotational force being applied to said actuator, said actuator moves either one of said fist arm, said second arm, or said actuation member and, upon movement of either one of said first arm, said second arm or said actuation member said first finger, said second finger, and said third finger move substantially simultaneously between said closed and open configurations while said axis of rotation having a fixed spatial relationship relative to said plane of tissue retraction.

2. A surgical tool as recited in claim 1, wherein said third finger is attached to said actuation member generally adjacent a free end portion thereof, said third finger moving substantially together with said actuation member.

3. A surgical tool as recited in claim 2, wherein said first, second and third fingers being configured to retract said body tissue in a direction substantially aligned with each of said fingers respective movement direction between said closed and open configurations.

4. A surgical tool as recited in claim 2, wherein at least one of said first, second or third fingers extends respectively from said first arm, said second arm or said actuation member in a direction substantially normal to said plane of tissue retraction.

5. A surgical tool as recited in claim 3, wherein at least one of said first, second, or third fingers is pivotally connected respectively to said first arm, said second arm, or said actuation member.

6. A surgical tool as recited in claim 4, wherein said first, second and third fingers form a radius of retraction, said radius of retraction increasing in magnitude as said first, second, and third fingers move substantially simultaneously between said closed and open configurations.

7. A surgical tool as recited in claim 3, further comprising a housing, said housing configured to at lest partially enclose a portion of said actuation member.

8. A surgical tool as recited in claim 7, wherein said housing is generally elongate and extending between a first and second housing end, said actuator provided generally adjacent said first housing end, said first and second arms provided generally adjacent said second housing end, whereby, said actuator being actuated remotely from said first, second, and third fingers.

9. A surgical tool as recited in claim 7, wherein said housing is provided with a holding portion, said holding portion being configured to hold said surgical tool in a desired spatial relationship relative to a substantially stable surgical platform.

10. A surgical tool as recited in claim 2, further comprising a first connecting arm and a second connecting arm, said first and second connecting arms being pivotally coupled at longitudinal ends thereof to said actuation member and respectively to said first and second pivoting arms;
whereby when said rotational force is applied to said single actuator, said actuator moves said actuation member while said actuation member cooperating with either one of said first or second connecting arms for moving said first pivoting arm, said second pivoting arm, and said actuation member between said closed and open configuration.

11. A surgical tool as recited in claim 10, wherein said single actuator being mechanically coupled to said actuation member, and said actuation member being movable relative to said first pivoting arm and said second pivoting arm generally along a translation axis.

12. A surgical tool as recited in claim 11, wherein said first and second pivoting arms are pivotable about a common pivoting axis, said pivoting axis being located generally in register with said translation axis and extending in a generally perpendicular orientation relative thereto.

13. A surgical tool as recited in claim 12, wherein said first and second connecting arms transforming said movement of actuation member along said translation axis into substantially equal and opposed pivoting motion between said first and second pivoting arms.

14. A surgical tool as recited in claim 11, wherein said first, second and third fingers being configured to retract said body tissue in a direction substantially aligned with each of said fingers respective movement direction between said closed and open configurations.

15. A surgical tool as recited in claim 10, wherein at least one of said first, second, or third fingers is pivotally connected respectively to said first arm, said second arm, or said actuation member.

16. A surgical tool as recited in claim 15, wherein at least one of said first, second or third fingers extends respectively from said first arm, said second arm or said actuation member in a direction substantially normal to said plane of tissue retraction.

17. A surgical tool as recited in claim 15, wherein said first, second and third fingers form a radius of retraction, said radius of retraction increasing in magnitude as said first, second, and third fingers move substantially simultaneously between said closed and open configurations.

18. A surgical tool as recited in claim 14, wherein at least one of said first, second or third fingers is provided with a friction enhancing texture for promoting substantially adherent contact with said body tissue being retracted.

19. A surgical tool as recited in claim 14, wherein at least one of said first, second or third fingers is provided with at least one suction aperture extending therethrough whereby said at least one suction aperture allows pneumatic coupling thereof to a suctioning device for allowing a suctioning action through said suction aperture.

20. A surgical tool as recited in claim 11, further comprising a housing, said housing configured to at least partially enclose a portion of said actuation member.

21. A surgical tool as recited in claim 20, wherein said housing is generally elongate and extending between a first and second housing end, said actuator provided generally adjacent said first housing end, said first and second arms provided generally adjacent said second housing end, whereby said actuator being actuated remotely from said first, second, and third fingers.

22. A surgical tool as recited in claim 21, wherein said actuator includes an actuation knob, and said movement of said actuation member is obtained by a rotation to said actuation knob.

23. A surgical tool as recited in claim 20, wherein said actuation member includes a flexible cable member.

24. A surgical tool as recited in claim 23, wherein said first and second pivoting arms are pivotable about a common pivoting axis, and wherein said first and second pivoting arms and said first and second connecting arms collectively as a linkage arrangement are pivotable relative to said common pivoting axis by virtue of said flexible cable member.

25. A surgical tool as recited in claim 11, further comprising an elongated tubular member having a rod channel extending longitudinally therethrough, said tubular member defining a tube first end and a longitudinally opposed tube second end, said first pivoting arm and said second pivoting arm being pivotally attached to said tubular member adjacent said tube first end, said actuation member including a cable slidably mounted within said rod channel, said cable defining a cable first end and an opposed cable second end, said cable first end being attached to said third finger generally adjacent said tube first end and said cable second end being attached to said actuator generally adjacent said tube second end whereby said actuator allows slidable movement of said cable within said rod channel and corresponding movement of said first finger, said second finger, and said third finger between said closed and open configurations.

26. A surgical tool as recited in claim 10, wherein said surgical tool is an atrial tissue retractor, and wherein said first, second, and third fingers being configured and sized for retracting atrial tissue during cardiac surgery.

27. A surgical tool a recited in claim 17, wherein said surgical tool is an aortic tissue retractor, and wherein said first, second, and third fingers being configured and sized for retracting aortic tissue during cardiac surgery.

28. A surgical tool as recited in claim 10, further comprising a positioning arm, said positioning arm configured for holding said surgical tool in a substantially stable spatial relationship relative to said patient while said body tissue is being retracted, wherein said positioning arm holds said surgical tool while said first and second pivoting arms move between said closed and open configuration.

29. A surgical tool as recited in claim 28, further comprising a surgical platform, said surgical platform for mounting said positioning arm in said spatial relationship relative to said patient while said body tissue is being retracted.

* * * * *